(12) United States Patent
Behzadi

(10) Patent No.: US 10,905,456 B2
(45) Date of Patent: Feb. 2, 2021

(54) BONE PREPARATION APPARATUS AND METHOD

(71) Applicant: Kambiz Behzadi, Pleasanton, CA (US)

(72) Inventor: Kambiz Behzadi, Pleasanton, CA (US)

( * ) Notice: Subject to any disclaimer, the term of this patent is extended or adjusted under 35 U.S.C. 154(b) by 100 days.

(21) Appl. No.: 16/276,639

(22) Filed: Feb. 15, 2019

(65) Prior Publication Data

US 2019/0343548 A1 Nov. 14, 2019

Related U.S. Application Data

(63) Continuation of application No. 15/398,996, filed on Jan. 5, 2017, now Pat. No. 10,251,663, which is a continuation-in-part of application No. 15/202,434, filed on Jul. 5, 2016.

(60) Provisional application No. 62/277,294, filed on Jan. 11, 2016.

(51) Int. Cl.
| | |
|---|---|
| *A61B 17/32* | (2006.01) |
| *A61B 17/16* | (2006.01) |
| *A61B 17/14* | (2006.01) |
| *A61F 2/46* | (2006.01) |

(52) U.S. Cl.
CPC .... *A61B 17/320068* (2013.01); *A61B 17/142* (2016.11); *A61B 17/1659* (2013.01); *A61B 17/1666* (2013.01); *A61B 17/1668* (2013.01); *A61B 17/1675* (2013.01); *A61F 2/4609* (2013.01); *A61B 2017/320082* (2017.08); *A61F 2002/4632* (2013.01); *A61F 2002/4662* (2013.01); *A61F 2002/4666* (2013.01); *A61F 2002/4681* (2013.01); *A61F 2002/4683* (2013.01)

(58) Field of Classification Search
CPC ........ A61B 17/320068; A61B 17/1659; A61B 17/1668
See application file for complete search history.

(56) References Cited

U.S. PATENT DOCUMENTS

| | | |
|---|---|---|
| 1,455,621 A | 5/1923 | Joyner |
| 2,121,193 A | 6/1938 | Paul |
| 3,818,514 A | 6/1974 | Clark |
| 4,135,517 A | 1/1979 | Reale |
| 4,457,306 A | 7/1984 | Borzone |
| 4,530,114 A | 7/1985 | Tepic |
| 4,712,951 A | 12/1987 | Brown |

(Continued)

FOREIGN PATENT DOCUMENTS

| | | |
|---|---|---|
| EP | 1433445 A1 | 6/2004 |
| WO | 2017029173 A1 | 2/2017 |
| WO | 2018031752 A1 | 2/2018 |

OTHER PUBLICATIONS

International Search Report for International application No. PCT/US2017/012753, dated May 5, 2017.

(Continued)

*Primary Examiner* — Christian A Sevilla
(74) *Attorney, Agent, or Firm* — Patent Law Offices of Michael E. Woods; Michael E. Woods

(57) ABSTRACT

A system and method for improving installation of a prosthesis. Devices include prosthesis installation tools, prosthesis assembly tools, site preparation systems, and improved power tools used in implant site preparation, the tools including a secondary motion that preferably includes an ultrasonic vibration.

11 Claims, 17 Drawing Sheets

(56) References Cited

U.S. PATENT DOCUMENTS

| | | | |
|---|---|---|---|
| 5,108,400 A | 4/1992 | Appel et al. | |
| 5,133,765 A | 7/1992 | Cuilleron | |
| 5,318,570 A * | 6/1994 | Hood | A61B 17/8847 606/99 |
| 5,534,006 A | 7/1996 | Szabo et al. | |
| 5,665,091 A * | 9/1997 | Noble | A61B 17/1659 606/79 |
| 5,769,092 A | 6/1998 | Williamson, Jr. | |
| 5,806,518 A | 9/1998 | Mittelstadt | |
| 5,849,015 A | 12/1998 | Haywood et al. | |
| 5,980,528 A | 11/1999 | Salys | |
| 6,110,179 A | 8/2000 | Flivik et al. | |
| 6,161,545 A | 12/2000 | Chow | |
| 6,204,592 B1 * | 3/2001 | Hur | A61B 17/1624 310/323.18 |
| 6,585,771 B1 | 7/2003 | Buttermilch et al. | |
| 7,036,211 B1 | 5/2006 | Panks | |
| 8,167,823 B2 | 5/2012 | Nycz et al. | |
| 8,603,100 B2 | 12/2013 | Muller | |
| 9,999,518 B2 | 6/2018 | Mani et al. | |
| 10,251,663 B2 | 4/2019 | Behzadi | |
| 2002/0183851 A1 | 12/2002 | Spiegelberg et al. | |
| 2003/0065398 A1 | 4/2003 | Cueille et al. | |
| 2003/0229357 A1 | 12/2003 | Dye | |
| 2005/0101962 A1 | 5/2005 | Schwenke et al. | |
| 2005/0154398 A1 | 7/2005 | Miniaci et al. | |
| 2006/0015110 A1 | 1/2006 | Pepper | |
| 2006/0142754 A1 | 6/2006 | Irion et al. | |
| 2007/0005144 A1 | 1/2007 | Leisinger et al. | |
| 2007/0162038 A1 | 7/2007 | Tuke | |
| 2007/0233131 A1 * | 10/2007 | Song | A61B 17/1671 606/79 |
| 2009/0192626 A1 | 7/2009 | Keefer et al. | |
| 2010/0023014 A1 * | 1/2010 | Romagnoli | A61B 17/164 606/85 |
| 2010/0249796 A1 | 9/2010 | Nycz | |
| 2011/0004318 A1 | 1/2011 | Tulkis et al. | |
| 2011/0178521 A1 | 7/2011 | Siravo et al. | |
| 2011/0264009 A1 | 10/2011 | Walter et al. | |
| 2012/0172939 A1 | 7/2012 | Pedicini | |
| 2012/0209277 A1 | 8/2012 | Leparmentier et al. | |
| 2013/0204264 A1 | 8/2013 | Mani et al. | |
| 2013/0211535 A1 | 8/2013 | Cueille | |
| 2013/0226189 A1 | 8/2013 | Young | |
| 2014/0135773 A1 | 5/2014 | Stein et al. | |
| 2014/0135791 A1 | 5/2014 | Nikou et al. | |
| 2015/0182350 A1 | 7/2015 | Behzadi | |
| 2015/0182351 A1 | 7/2015 | Behzadi | |
| 2015/0196343 A1 | 7/2015 | Donald et al. | |
| 2015/0201918 A1 | 7/2015 | Kumar et al. | |
| 2015/0282856 A1 | 10/2015 | Haiat et al. | |
| 2016/0166390 A1 | 6/2016 | Dye et al. | |
| 2016/0206430 A1 | 7/2016 | Grostefon et al. | |
| 2016/0206433 A1 | 7/2016 | Grostefon et al. | |
| 2016/0220315 A1 | 8/2016 | Falardeau et al. | |
| 2017/0056205 A1 | 3/2017 | Biegun et al. | |
| 2017/0196506 A1 | 7/2017 | Behzadi | |
| 2017/0196701 A1 | 7/2017 | Behzadi et al. | |
| 2017/0196704 A1 | 7/2017 | Behzadi et al. | |
| 2017/0196705 A1 | 7/2017 | Behzadi | |
| 2017/0196706 A1 | 7/2017 | Behzadi | |
| 2017/0196707 A1 | 7/2017 | Behzadi | |
| 2017/0196708 A1 | 7/2017 | Behzadi et al. | |
| 2017/0196710 A1 | 7/2017 | Behzadi | |
| 2017/0196711 A1 | 7/2017 | Behzadi | |
| 2017/0325972 A1 | 11/2017 | Steif | |
| 2017/0340456 A1 | 11/2017 | Behzadi | |
| 2018/0049891 A1 | 2/2018 | Termanini | |
| 2018/0235764 A1 | 8/2018 | Moore et al. | |
| 2018/0235765 A1 | 8/2018 | Welker et al. | |

OTHER PUBLICATIONS

Written Opinion of the International Searching Authority for International application No. PCT/US2017/012753 dated May 5, 2017.
International Search Report for International application No. PCT/US2017/046261, dated Oct. 18, 2017.
Written Opinion of the International Searching Authority for International application No. PCT/US2017/046261, dated Oct. 18, 2017.

* cited by examiner

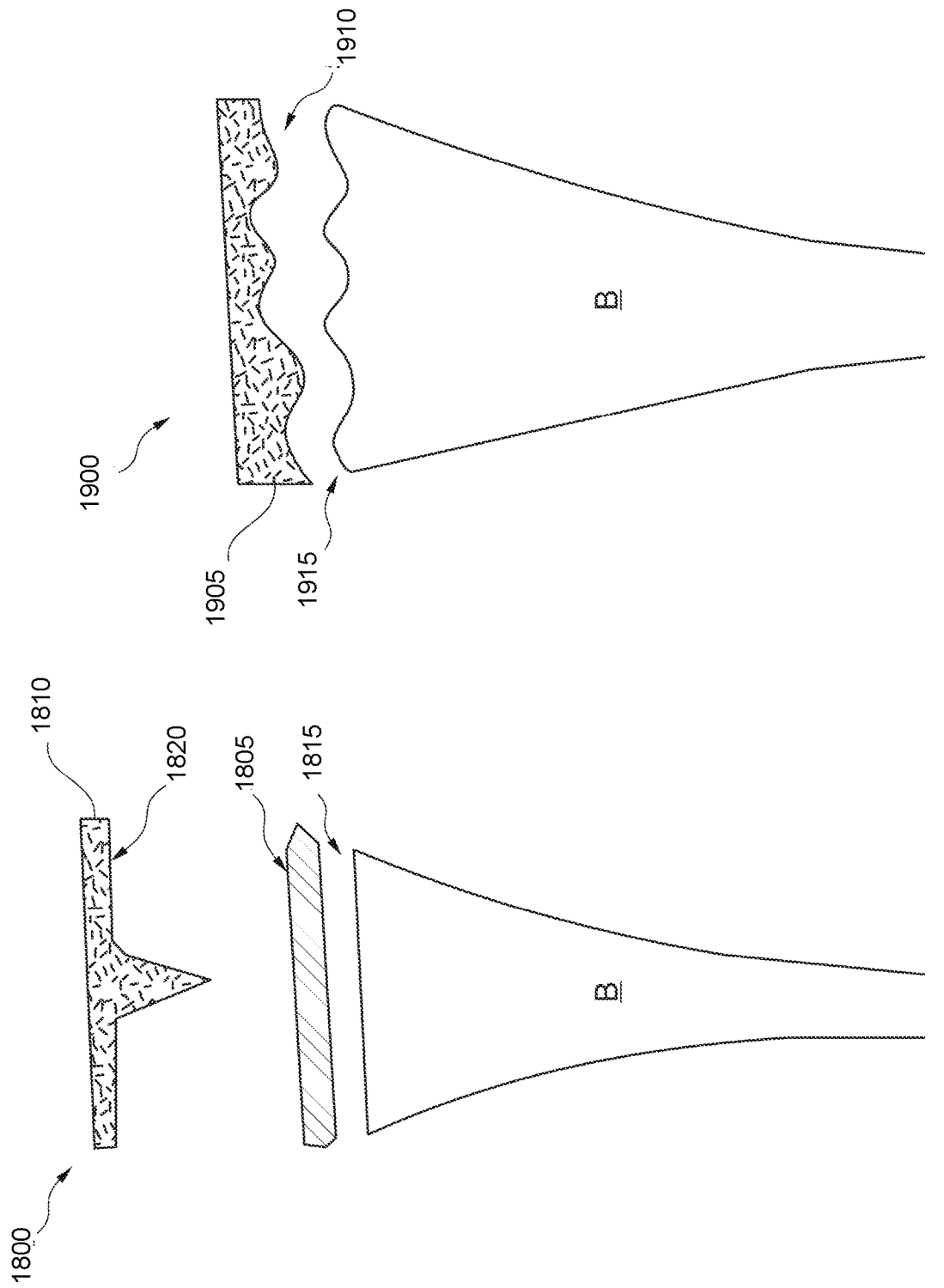

BONE PREPARATION APPARATUS AND METHOD

CROSS REFERENCE TO RELATED APPLICATIONS

This application is a Continuation of application Ser. No. 15/398,996 filed on Jan. 5, 2017; application Ser. No. 15/398,996 is a Continuation-in-part of application Ser. No. 15/202,434 filed on Jul. 5, 2016; application Ser. No. 15/202,434 claims the benefit of U.S. Provisional Application 62/277,294 filed on Jan. 11, 2016; all of which are hereby expressly incorporated in their entireties by reference thereto for all purposes.

FIELD OF THE INVENTION

The present invention relates generally to installation of a prosthesis, and more specifically, but not exclusively, to improvements in prosthesis placement and positioning.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Earlier patents issued to the present applicant have described problems associated with prosthesis installation, for example acetabular cup placement in total hip replacement surgery. See U.S. Pat. Nos. 9,168,154 and 9,220,612, which are hereby expressly incorporated by reference thereto in their entireties for all purposes. Even though hip replacement surgery has been one of the most successful operations, it continues to be plagued with a problem of inconsistent acetabular cup placement. Cup mal-positioning is the single greatest cause of hip instability, a major factor in polyethylene wear, osteolysis, impingement, component loosening and the need for hip revision surgery.

These incorporated patents explain that the process of cup implantation with a mallet is highly unreliable and a significant cause of this inconsistency. The patents note two specific problems associated with the use of the mallet. First is the fact that the surgeon is unable to consistently hit on the center point of the impaction plate, which causes undesirable torques and moment arms, leading to mal-alignment of the cup. Second, is the fact that the amount of force utilized in this process is non-standardized.

In these patents there is presented a new apparatus and method of cup insertion which uses an oscillatory motion to insert the prosthesis. Prototypes have been developed and continue to be refined and illustrate that vibratory force may allow insertion of the prosthesis with less force, as well, in some embodiments, of allowing simultaneous positioning and alignment of the implant.

There are other ways of breaking down of the large undesirable, torque-producing forces associated with the discrete blows of the mallet into a series of smaller, axially aligned controlled taps, which may achieve the same result incrementally, and in a stepwise fashion to those set forth in the incorporated patents, (with regard to, for example, cup insertion without unintended divergence).

There are two problems that may be considered independently, though some solutions may address both in a single solution. These problems include i) undesirable and unpredictable torques and moment arms that are related to the primitive method currently used by surgeons, which involves manually banging the mallet on an impaction plate mated to the prosthesis and ii) non-standardized and essentially uncontrolled and unquantized amounts of force utilized in these processes.

What is needed is a system and method for improving installation of a prosthesis.

BRIEF SUMMARY OF THE INVENTION

Disclosed is a system and method for improving installation of a prosthesis. The following summary of the invention is provided to facilitate an understanding of some of the technical features related to prosthesis assembly and installation and is not intended to be a full description of the present invention. A full appreciation of the various aspects of the invention can be gained by taking the entire specification, claims, drawings, and abstract as a whole. The present invention is applicable to other prosthesis in addition to acetabular cups, other modular prosthesis in addition to assembly of modular femoral and humeral prosthesis, and to other alignment and navigation systems in addition to referenced light guides.

An embodiment of the present invention may include axial alignment of force transference, such as, for example, an axially sliding hammer moving between stops to impart a non-torqueing installation force. There are various ways of motivating and controlling the sliding hammer, including a magnitude of transferred force. Optional enhancements may include pressure and/or sound sensors for gauging when a desired depth of implantation has occurred.

Other embodiments include adaptation of various devices for accurate assembly of modular prostheses, such as those that include a head accurately impacted onto a trunnion taper that is part of a stem or other element of the prosthesis.

Still other embodiments include an alignment system to improve site preparation, such as, for example, including a projected visual reference of a desired orientation of a tool and then having that reference marked and available for use during operation of the tool to ensure that the alignment remains proper throughout its use, such as during a reaming operation.

Further embodiments include enhancement of various tools, such as those used for cutting, trimming, drilling, and the like, with ultrasonic enhancement to make the device a better cutting, trimming, drilling, etc. device to enable its use with less strength and with improved accuracy.

A bone preparation tool, including a bone-processing implement configured to process an in-patient bone using a primary motion in a primary mode of freedom of motion; and a motive system, coupled to the cutting implement, configured to operate the cutting implement in the primary mode of freedom of motion and in a secondary mode of primary mode of freedom different from the primary mode of freedom wherein the secondary mode of freedom includes an ultrasonic vibratory motion.

A method for preparing an in-patient bone, including processing, using a bone-processing implement, the in-patient bone using a primary motion in a primary mode of freedom of motion for the a bone-processing implement; and concurrently operating the a bone-processing implement in a secondary motion including a secondary mode of freedom of motion; wherein the secondary mode of freedom is different than the primary mode of freedom of motion; and wherein the secondary motion includes an ultrasonic vibration motion.

A bone preparation tool, including a bone-processing implement configured to process an in-patient bone using a primary motion in a primary mode of freedom of motion; and a motive system, coupled to said cutting implement, configured to operate said bone-processing implement in said primary mode of freedom of motion and in a secondary mode of motion, wherein said primary mode of freedom includes a non-ultrasonic motion and wherein said secondary mode of freedom includes an ultrasonic vibratory motion superimposed on said non-ultrasonic motion.

A method for preparing an in-patient bone, including processing, using a bone-processing implement, the in-patient bone using a primary motion in a primary mode of freedom of motion for said a bone-processing implement; and concurrently operating said a bone-processing implement in a secondary motion including a secondary mode of freedom of motion; wherein said primary motion consists essentially of a non-ultrasonic motion; and wherein said secondary motion includes an ultrasonic vibration motion.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1 illustrates an embodiment of the present invention for a sliding impact device;

FIG. 2 illustrates a lengthwise cross-section of the embodiment illustrated in FIG. 1 including an attachment of a navigation device;

FIG. 3 illustrates a cockup mechanical gun embodiment, an alternative embodiment to the sliding impact device illustrated in FIG. 1 and FIG. 2;

FIG. 4 illustrates an alternative embodiment to the devices of FIG. 1-3 including a robotic structure;

FIG. 5 illustrates an alternative embodiment to the devices of FIG. 1-4 including a pressure sensor to provide feedback;

FIG. 6 illustrates an alternative embodiment to the feedback system of FIG. 5 including a sound sensor to provide feedback for the embodiments of FIG. 1-5;

FIG. 7 illustrates a modular prosthesis and assembly tools;

FIG. 8 illustrates a femoral head to be assembled onto a trunnion attached to a femoral stem;

FIG. 9 illustrates alignment of an installation device with the femoral head for properly aligned impaction onto the trunnion, such as an embodiment of FIG. 1-FIG. 6 adapted for this application;

FIG. 10 illustrates use of a modified vibratory system for assembly of the modular prosthesis;

FIG. 11 illustrates an environment in which a prosthesis is installed highlighting problem with site preparation; and FIG. 12 illustrates an alignment system for preparation and installation of a prosthesis;

FIG. 14 illustrates a perspective view of a powered bone saw;

FIG. 15 illustrates a broach attachment for a powered reciprocating bone preparation tool;

FIG. 16 illustrates a hand-operated reamer; and

FIG. 17 illustrates a set of bone preparation burrs;

FIG. 18 illustrates a side view of a first set of components for a conventional bone preparation process;

FIG. 19 illustrates a side view of a second set of components for a three-dimensional bone sculpting process that may be enabled by some embodiments of the present invention.

DETAILED DESCRIPTION OF THE INVENTION

Figure 1:
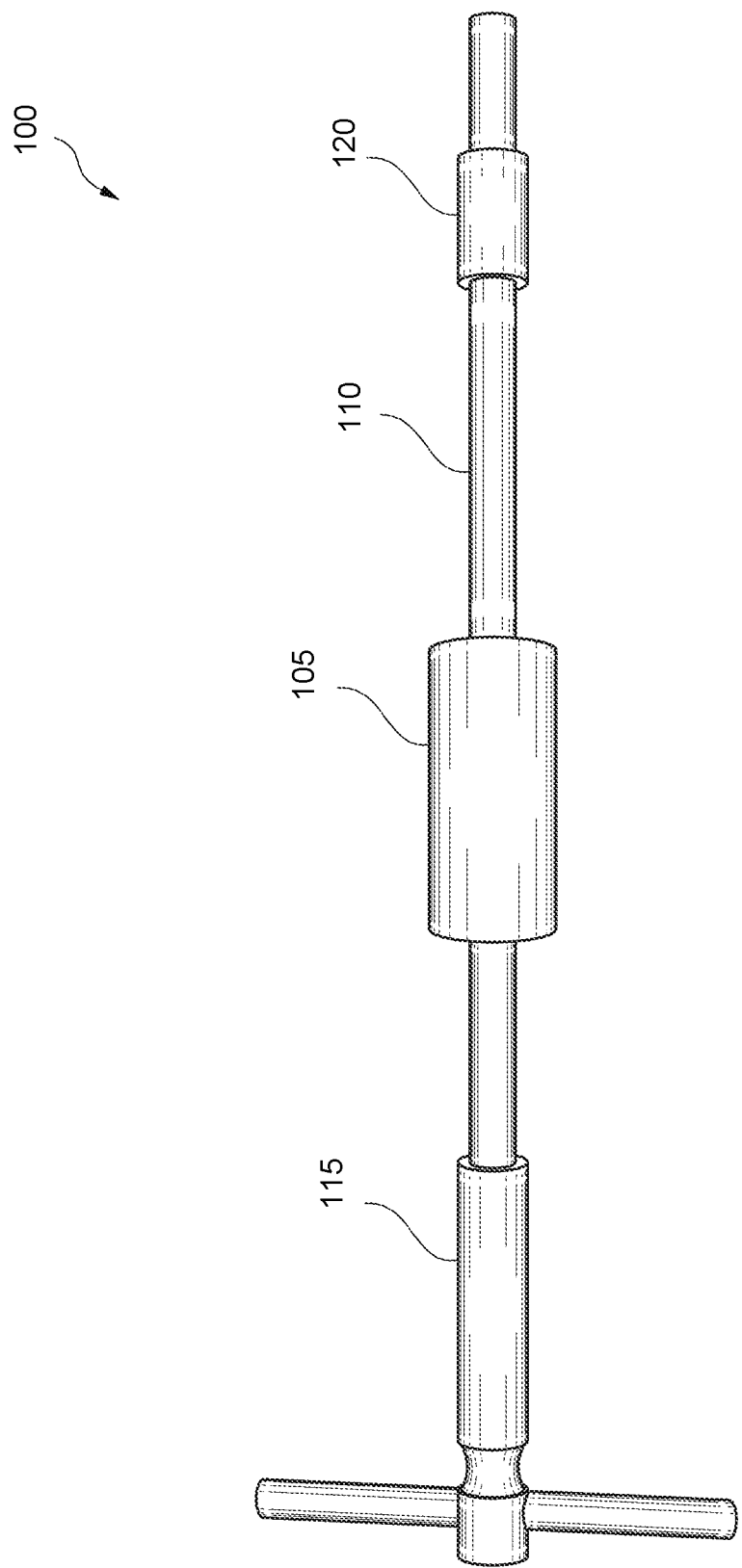
FIG. 1-FIG. 6 illustrate embodiments including installation of a prosthesis, including installation into living bone.

Embodiments of the present invention provide a system and method for improving installation of a prosthesis. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

Embodiments of the present invention may include one of more solutions to the above problems. The incorporated U.S. Pat. No. 9,168,154 includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques, and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine and in some cases a smart tool robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a structure (e.g., hollow cylindrical mass) that travels over a stainless rod.

Figure 2:
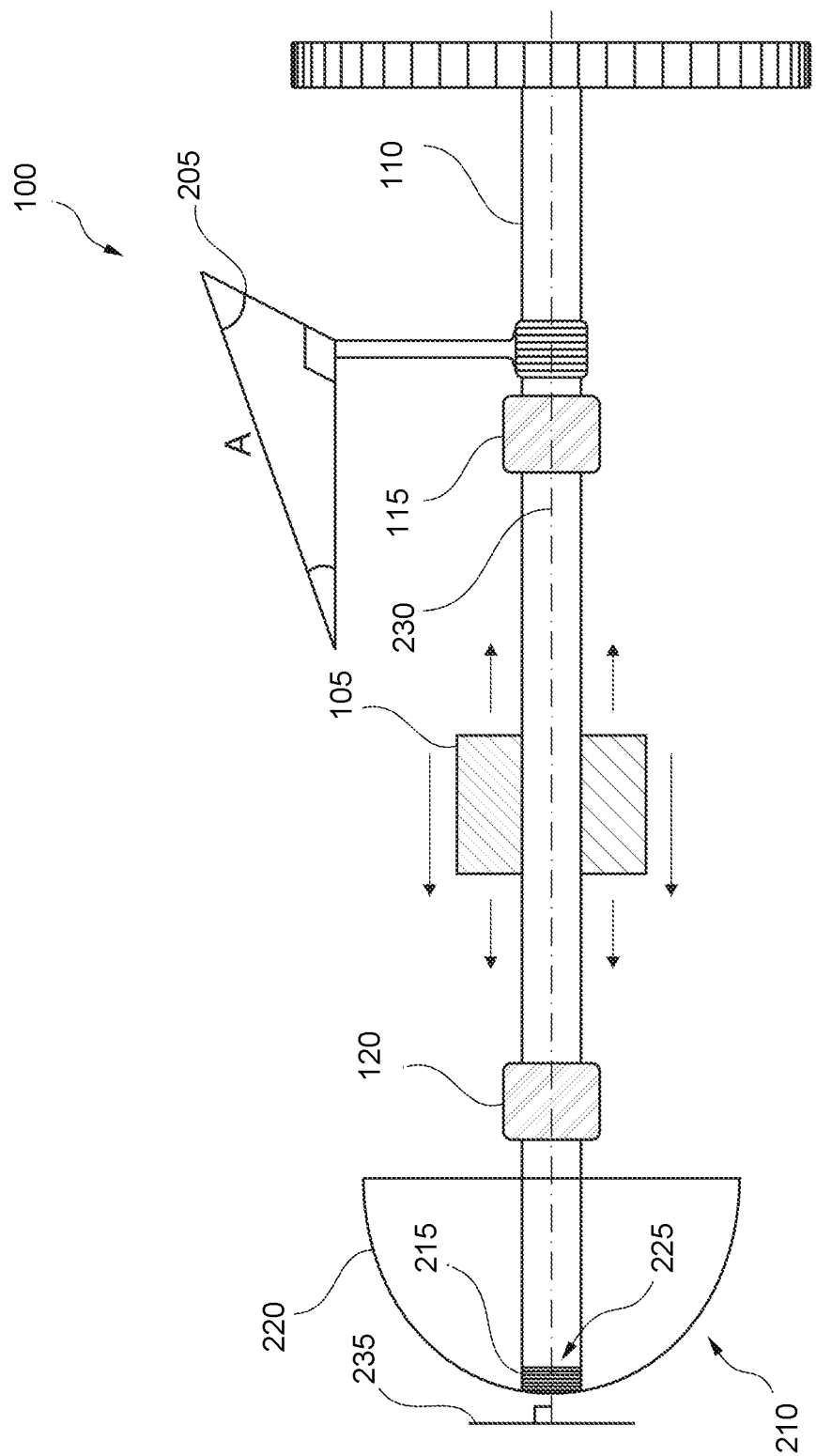

FIG. 1 illustrates an embodiment of the present invention for a sliding impact device 100, and FIG. 2 illustrates a lengthwise cross-section of sliding impact device 100 including an attachment of a navigation device 205.

Device 100 includes a moveable hammer 105 sliding axially and freely along a rod 110. Rod 110 includes a proximal stop 115 and distal stop 120. These stops that may be integrated into rod 110 to allow transference of force to rod 110 when hammer 105 strikes distal stop 120. At a distal end 210 of rod 110, device 100 includes an attachment system 215 for a prosthesis 220. For example, when prosthesis 220 includes an acetabular cup having a threaded cavity 225, attachment system 215 may include a complementary threaded structure that screws into threaded cavity 225. The illustrated design of device 100 allows only a perfect axial force to be imparted. The surgeon cannot deliver a blow to the edge of an impaction plate. Therefore, the design of this instrument is in and of itself protective, eliminating a problem of "surgeon's mallet hitting on the edge of the impaction plate" or other mis-aligned force transference, and creating undesirable torques, and hence unintentional mal-alignment of prosthesis 220 from an intended position/orientation.

A longitudinal axis 230 extends through the ends of rod 110. Attachment system 215 aligns prosthesis 220 to axis 230 when rod 110 is coupled to threaded cavity 225. An apex of prosthesis 220 (when it generally defines a hollow semi-spherical shell) supports a structure that defines threaded cavity 225 and that structure may define a plane 235 that may be tangent to the apex, with plane 235 about perpendicular to axis 230 when rod 110 engages prosthesis 220. Operation of device 100 is designed to deliver only axial (e.g., aligned with axis 230 and thus non-torqueing) forces to prosthesis 220. Other embodiments illustrated in FIG. 3-FIG. 6 may be similarly configured.

Figure 3:
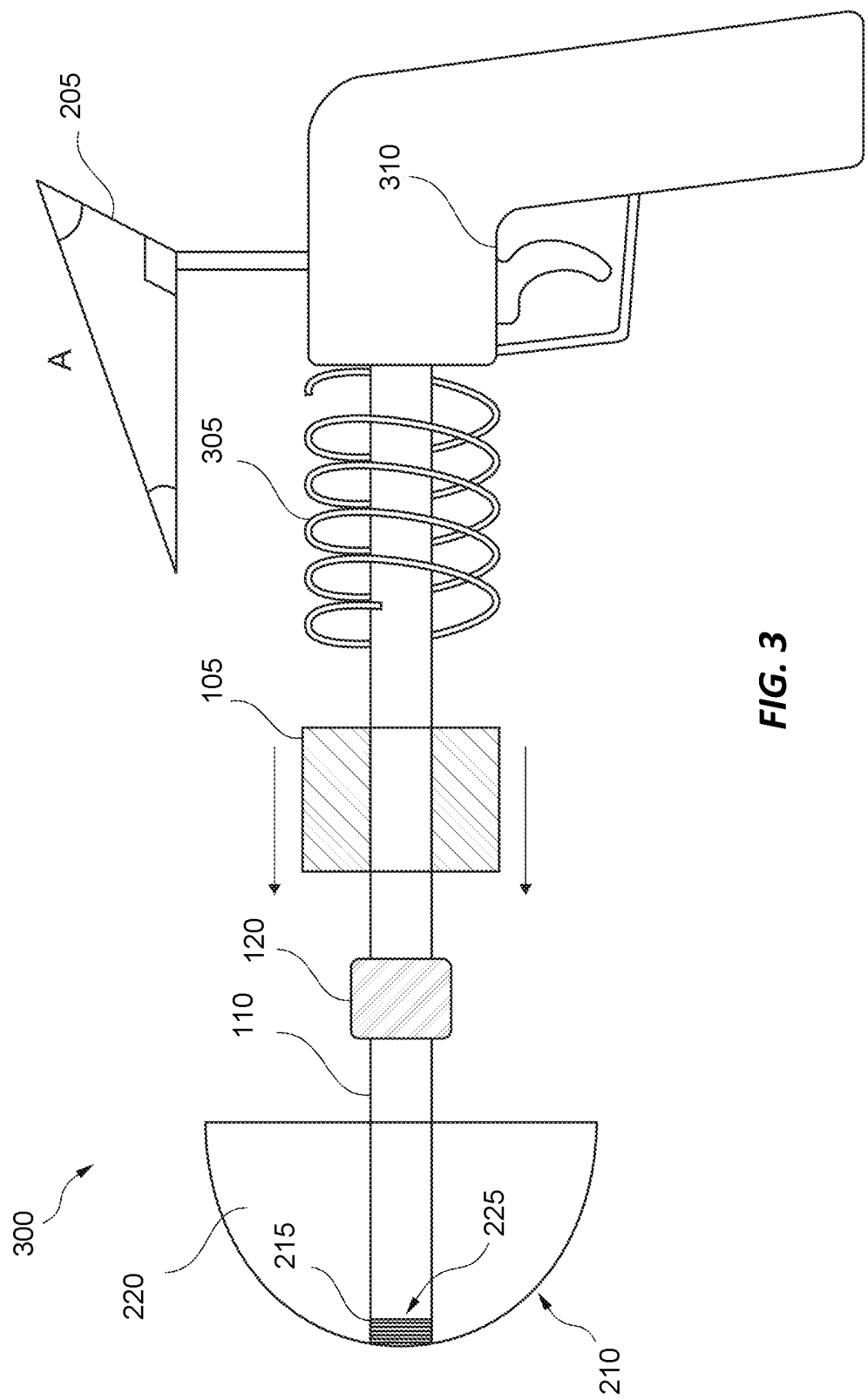

FIG. 3 illustrates a cockup mechanical gun 300 embodiment, an alternative embodiment to the sliding impact device illustrated in FIG. 1 and FIG. 2. An alternate embodiment includes cockup mechanical gun 300 that uses the potential energy of a cocked-up spring 305 to create an axially aligned impaction force. Hammer 105 is drawn back and spring 305 is locked until an operator actuates a trigger 310 to release spring 305 and drive hammer 105 along rod 110 to strike distal stop 120 and transfer an axially aligned impacting force to prosthesis 220.

Each pull of trigger 310 creates the same predetermined fixed unit of force (some alternatives may provide a variably predetermined force). The surgeon cannot deliver a mis-aligning impact to an impaction plate with this design.

Figure 4:
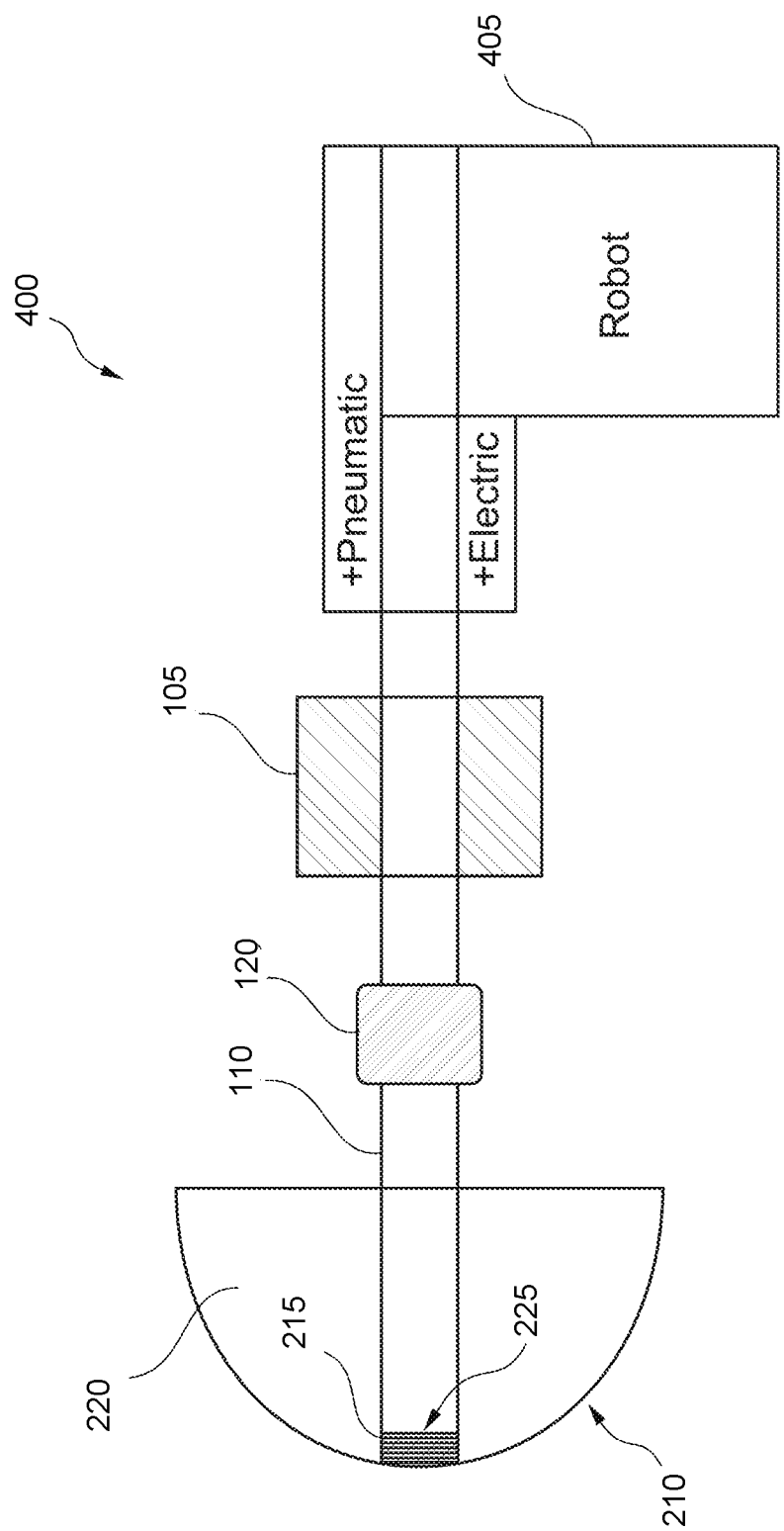

FIG. 4 illustrates an alternative robotic device 400 embodiment to the devices of FIG. 1-3 including a robotic control structure 405. For example, device 100 and/or device 300 may be mounted with robot control structure 405 and the co-axial impacts may be delivered mechanically by a robotic tool using pneumatic or electric energy.

Figure 5:
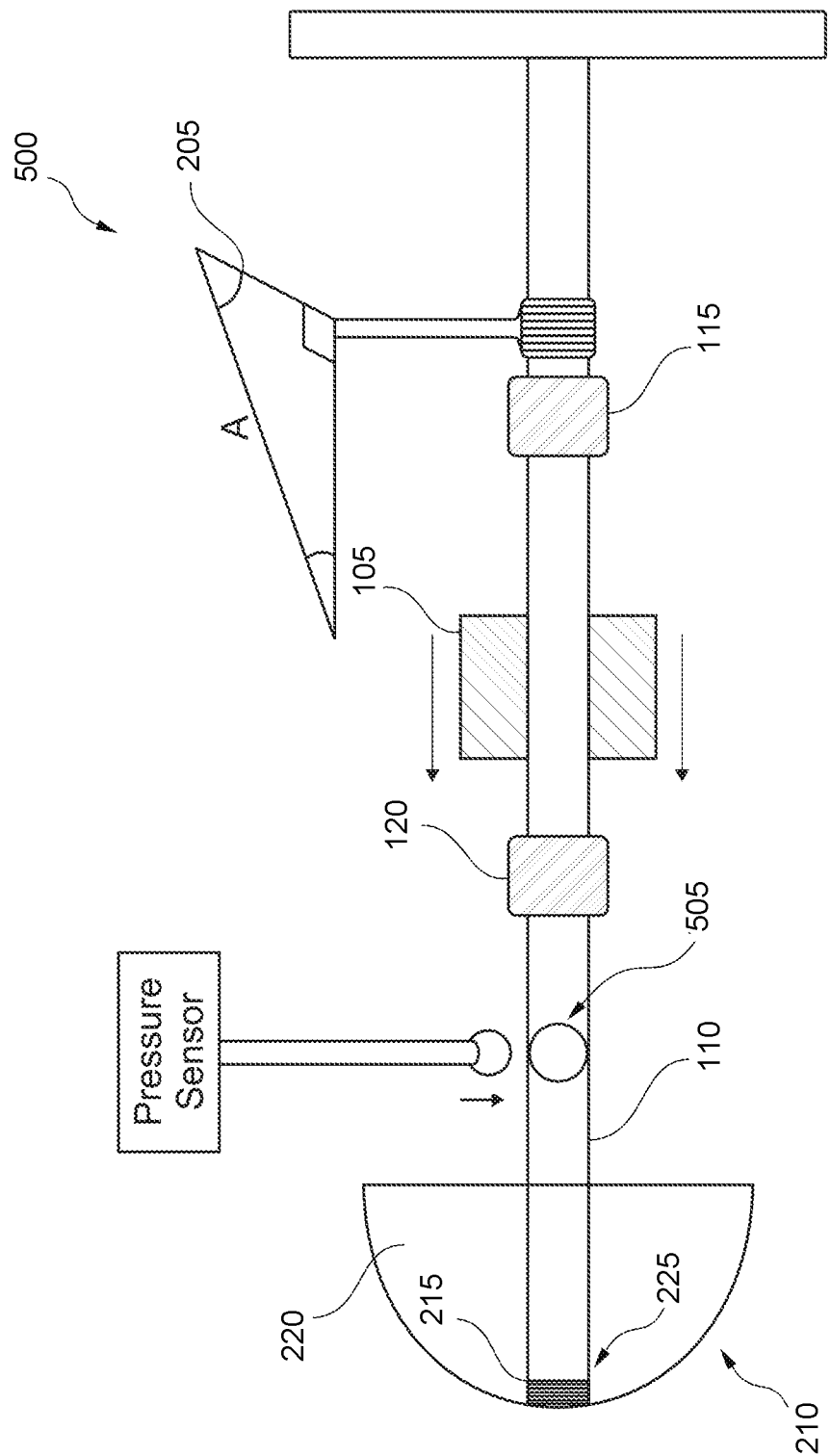

FIG. 5 illustrates an alternative embodiment 500 to the devices of FIG. 1-4 including a pressure sensor 505 to provide feedback during installation. With respect to management of the force required for some of these tasks, it is noted that with current techniques (the use of the mallet) the surgeon has no indication of how much force is being imparted onto the implant and/or the implant site (e.g., the pelvis). Laboratory tests may be done to estimate what range of force should be utilized in certain age groups (as a rough guide) and then fashioning a device 500, for example a modified sledgehammer 100 or cockup gun 300 to produce just the right amount of force. Typically, the surgeon may use up to 2000 N to 3000 N of force to impact a cup into the acetabular cavity. Also, since some embodiments cannot deliver the force in an incremental fashion as described in association with the BMD3 device, device 500 includes a stopgap mechanism. Some embodiments of the BMD3 device have already described the application of a sensor in the body of the impaction rod. Device 500 includes sensing system/assembly 505 embedded in device 500, for example proximate rod 110 near distal end 210, and used to provide valuable feedback information to the surgeon. Pressure sensor 505 can let the surgeon know when the pressures seems to have maximized, whether used for the insertion of an acetabular cup, or any other implant including knee and shoulder implants and rods used to fix tibia and femur fractures. When pressure sensor 505 is not showing an advance or increase in pressure readings and has plateaued, the surgeon may determine it is time to stop operation/impacting. An indicator, for example an alarm can go off or a red signal can show when maximal peak forces are repeatedly achieved. As noted above, the incorporated patents describe a presence of a pressure sensor in an installation device, the presence of which was designed as part of a system to characterize an installation pulse pattern communicated by a pulse transfer assembly. The disclosure here relates to a pressure sensor provided not to characterize the installation pulse pattern but to provide an in situ feedback mechanism to the surgeon as to a status of the installation, such as to reduce a risk of fracturing the installation site. Some embodiments may also employ this pressure sensor for multiple purposes including characterization of an applied pulse pattern such as, for example, when the device includes automated control of an impacting engine coupled to the hammer. Other embodiments of this invention may dispose the sensor or sensor reading system within a handle or housing of the device rather than in the central rod or shaft.

Figure 6:
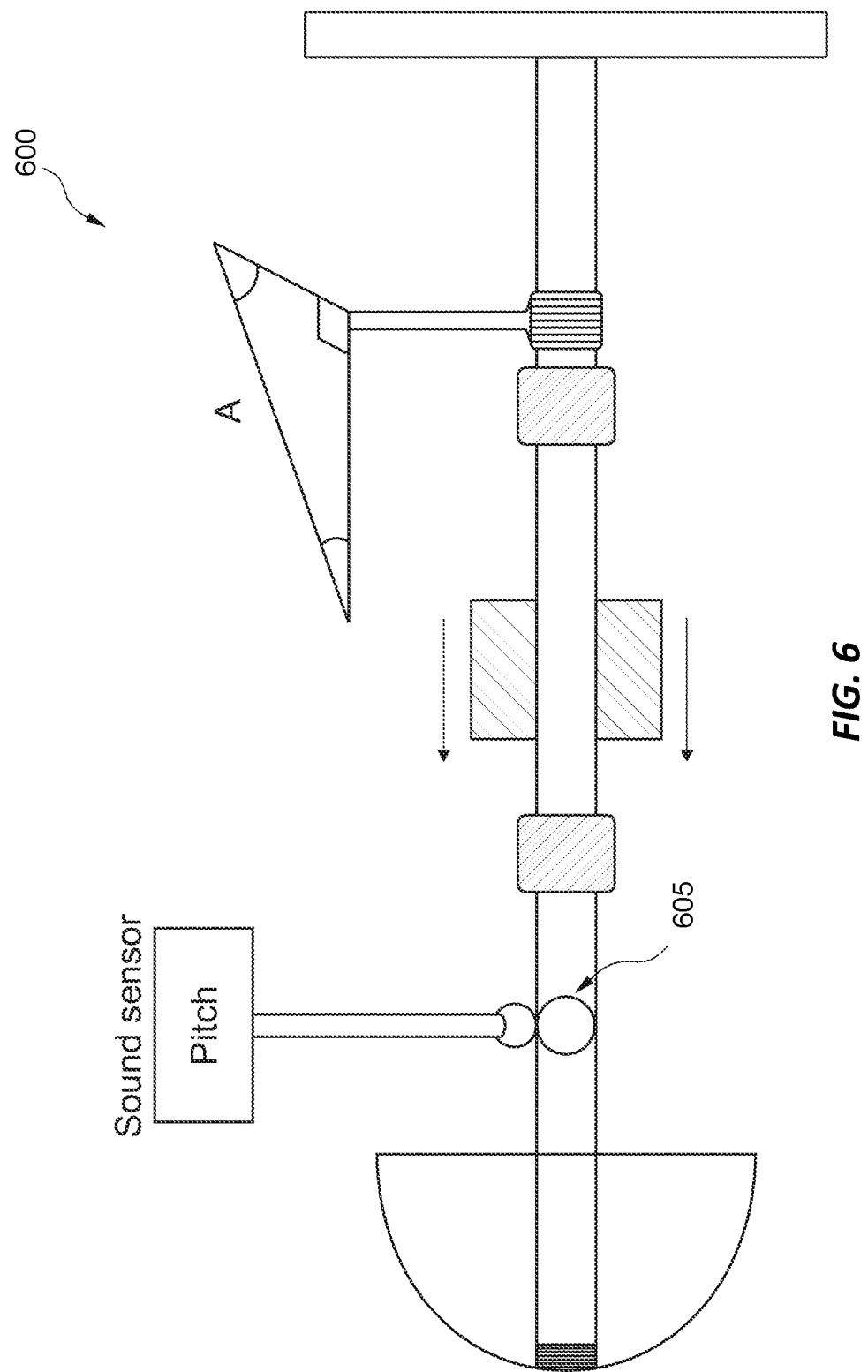

FIG. 6 illustrates an alternative device 600 embodiment to the feedback system of FIG. 5 including a sound sensor 605 to provide feedback for the embodiments of FIG. 1-5. Surgeons frequently use a change in pitch (sound) to gauge whether an implant (e.g., the cup) has "bottomed out" (an evaluation of a "seatedness" of the implant) and device 600 includes sound sensor 605 either attached or coupled to rod 110 or otherwise disposed separately in the operating room. Sound sensor system/assembly 605 may be used in lieu of, or in addition to, pressure sensor system/assembly 505 illustrated in FIG. 5.

Figure 7:
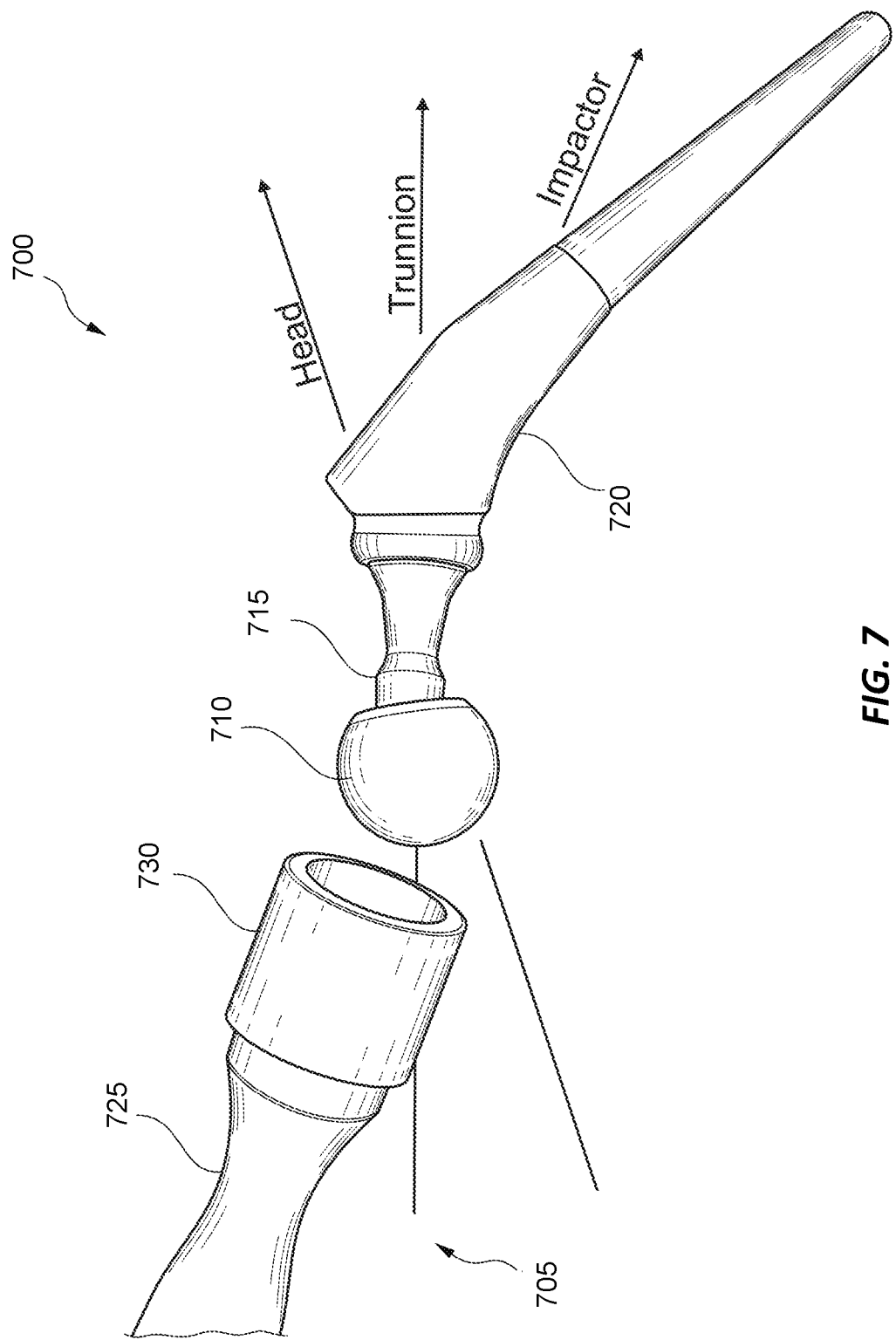
FIG. 7-FIG. 10 illustrate prosthesis assembly embodiments including use of variations of the prosthesis installation embodiments of FIG. 1-FIG. 6, such as may be used to reduce a risk of trunnionosis.

FIG. 7-FIG. 10 illustrate prosthesis assembly embodiments including use of variations of the prosthesis installation embodiments of FIG. 1-FIG. 6, such as may be used to reduce a risk of trunnionosis or for other advantage. FIG. 7 illustrates a modular prosthesis 700 and assembly tool 705. Prosthesis 700 includes a head 710 and a trunnion taper 715 at an end of a stem 720 (e.g., a femoral stem for supporting a ball head to fit within an acetabular cup used in a total hip replacement procedure). During the procedure, the surgeon assembles prosthesis 700 by using tool 705 which may include an impact rod 725 attached to a head coupler 730. The surgeon uses tool 705 to drive head 710 onto trunnion taper 715 which conventionally includes a free mallet striking tool 705. Such a procedure may be prone to the similar problems as installation of a prosthesis into an implant site, namely application of off-axis torqueing forces and an uncertainty of applied force and completion of assembly.

It is believed that even a 0.1 degree mal-alignment on head 710 on trunnion taper 715 may lead to progressive wear and metalosis. Variations of the embodiments of devices illustrated in FIG. 1-FIG. 6 and its associated content may be developed to help resolve this problem. In the case of "non-torqueing axiality" of forces from an assembly device, a bore of the head may define an axis, the trunnion taper may define an axis, with the assembly device aligning these axes and then applying its forces in co-axial alignment with these co-axially aligned axes. Such an embodiment may reduce or eliminate any force-responsive rotations of the head with respect to the taper as the head is seated into position by the assembly device.

Figure 8:
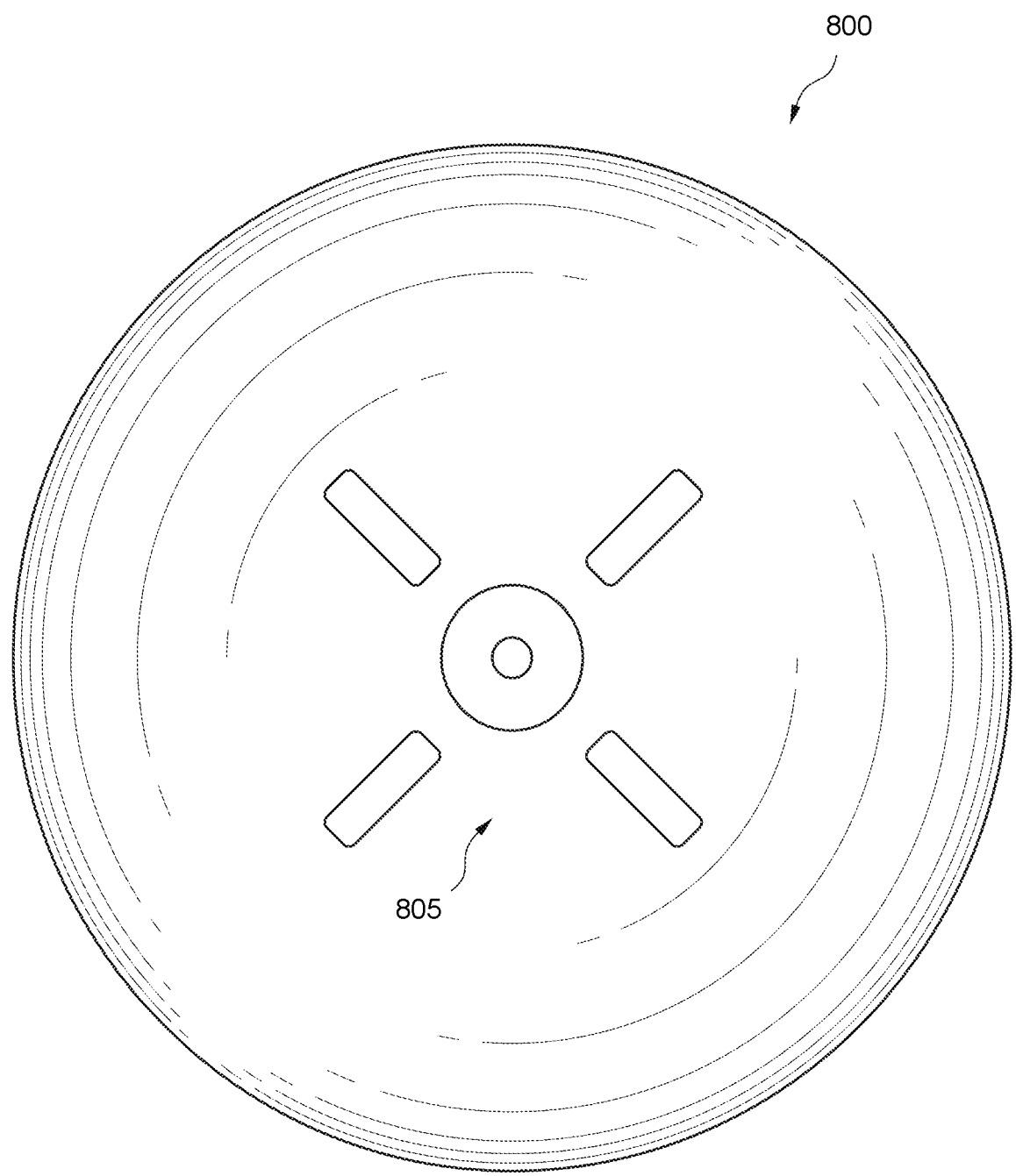

FIG. 8 illustrates a femoral head 805, a variation of head 710 illustrated in FIG. 7, to be assembled onto trunnion taper 715 that is coupled to femoral stem 720. A center dot 810 may be placed on femoral (or humeral) head 805 to be impacted using tool 705.

Figure 9:
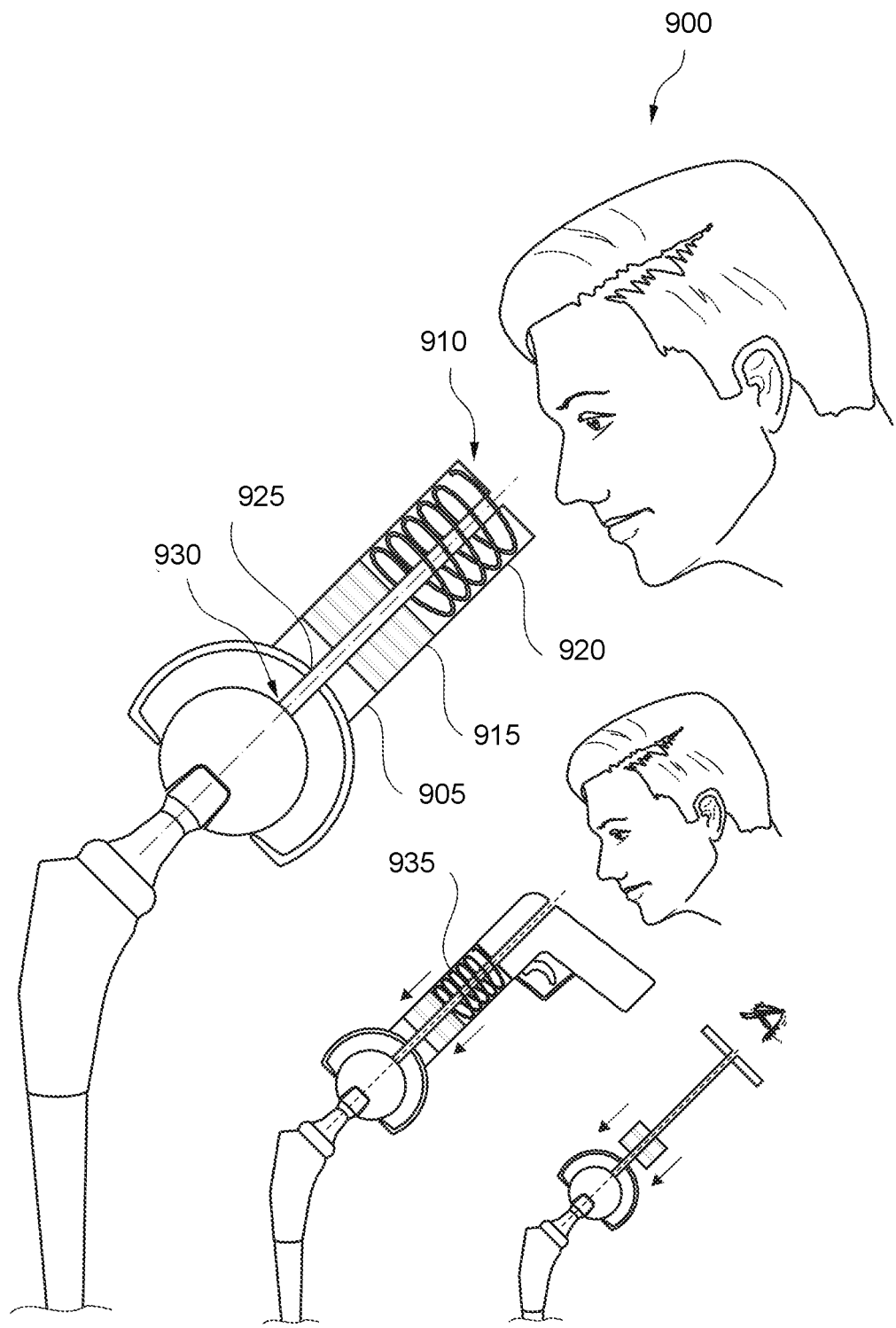

FIG. 9 illustrates alignment of an installation device 900, a variation of any of devices 100-600, with femoral head 805 for properly aligned impaction onto trunnion taper 715, such as an embodiment of FIG. 1-FIG. 6 adapted for this application. Such adaptation may include, for example, an axial channel 910 to view dot 810, and align force transference, prior to operation of hammer 105. Device 900 includes a sledgehammer 915 and a cock-up spring to drive sledgehammer 915. A slot 925 allows an operator to visualize a centering mark 930. A spring-loaded structure 935 may be used to operate a device.

Dot 810 can be aligned with an impactor/device/gun. Once axial alignment, such as through the sight channel, has been confirmed, a sledgehammer, a cockup gun, or other similar device can bang the impactor onto femoral (humeral) head 805 to impact it on trunnion taper 715. The co-axiality of the head and the device can be confirmed visually (for example, through a hollow cylinder that comprises a center shaft of the device) or with a variety of electronic and laser methods.

Figure 10:
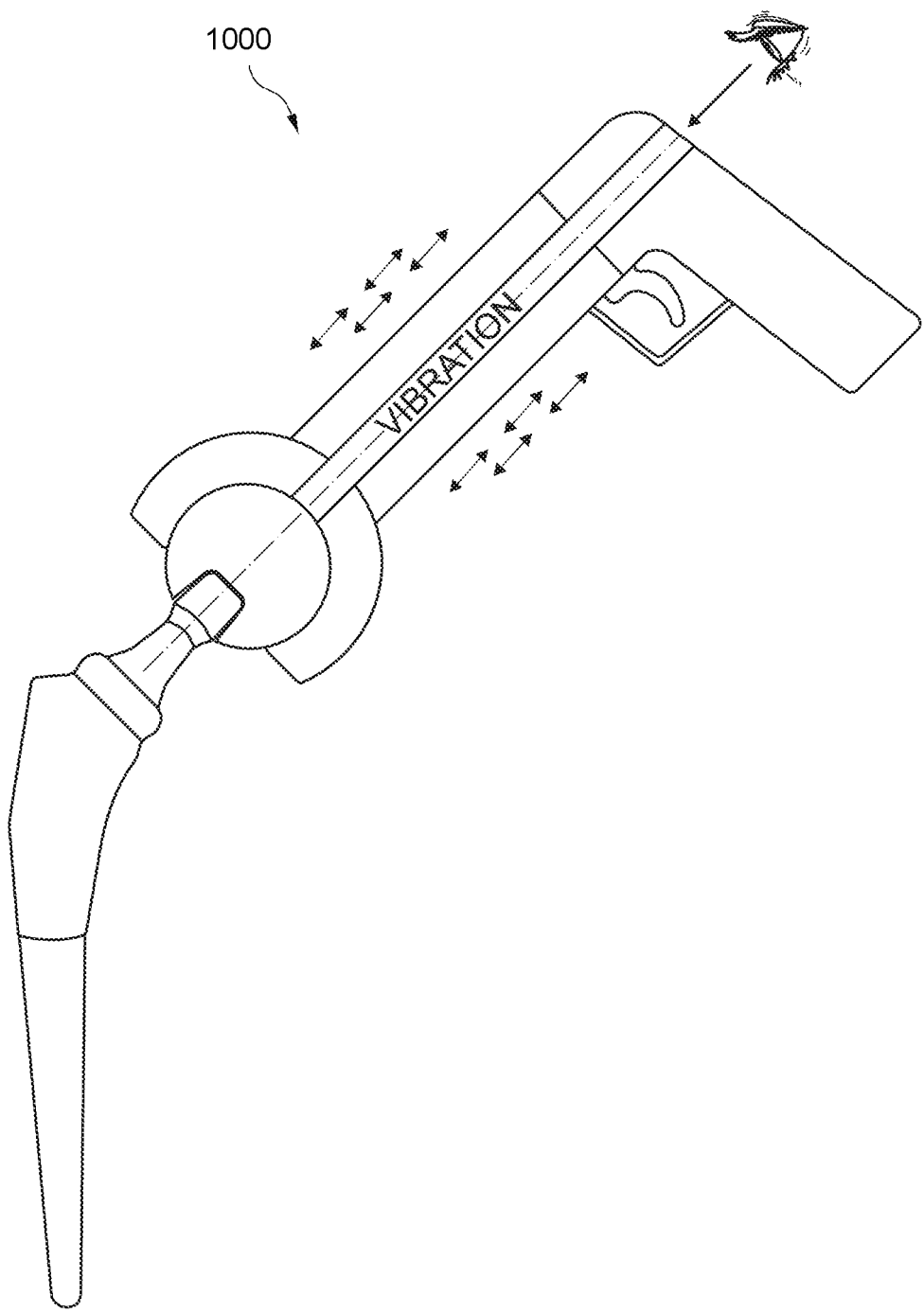

FIG. 10 illustrates use of a modified vibratory system 1000, a variation of installation device 900 for assembly of the modular prosthesis illustrated in FIG. 7. Alternatively, to device 900, a variation of the BMD3 device can be used to insert the femoral and humeral heads 710 onto trunnion taper 715. For example, a version of the BMD3 device where femoral head 710 is grasped by a "vibrating gun" and introduced methodically and incrementally onto trunnion taper 715. Since there are no large forces being applied to the head/trunnion junction, there is essentially no possibility, or a reduced possibility, of head 710 seating onto trunnion taper 715 in a misaligned fashion. It would be possible to use the same technique of marking the center of head 710 and lining it up with trunnion taper 715 and device axially before operating the device.

Figure 11:
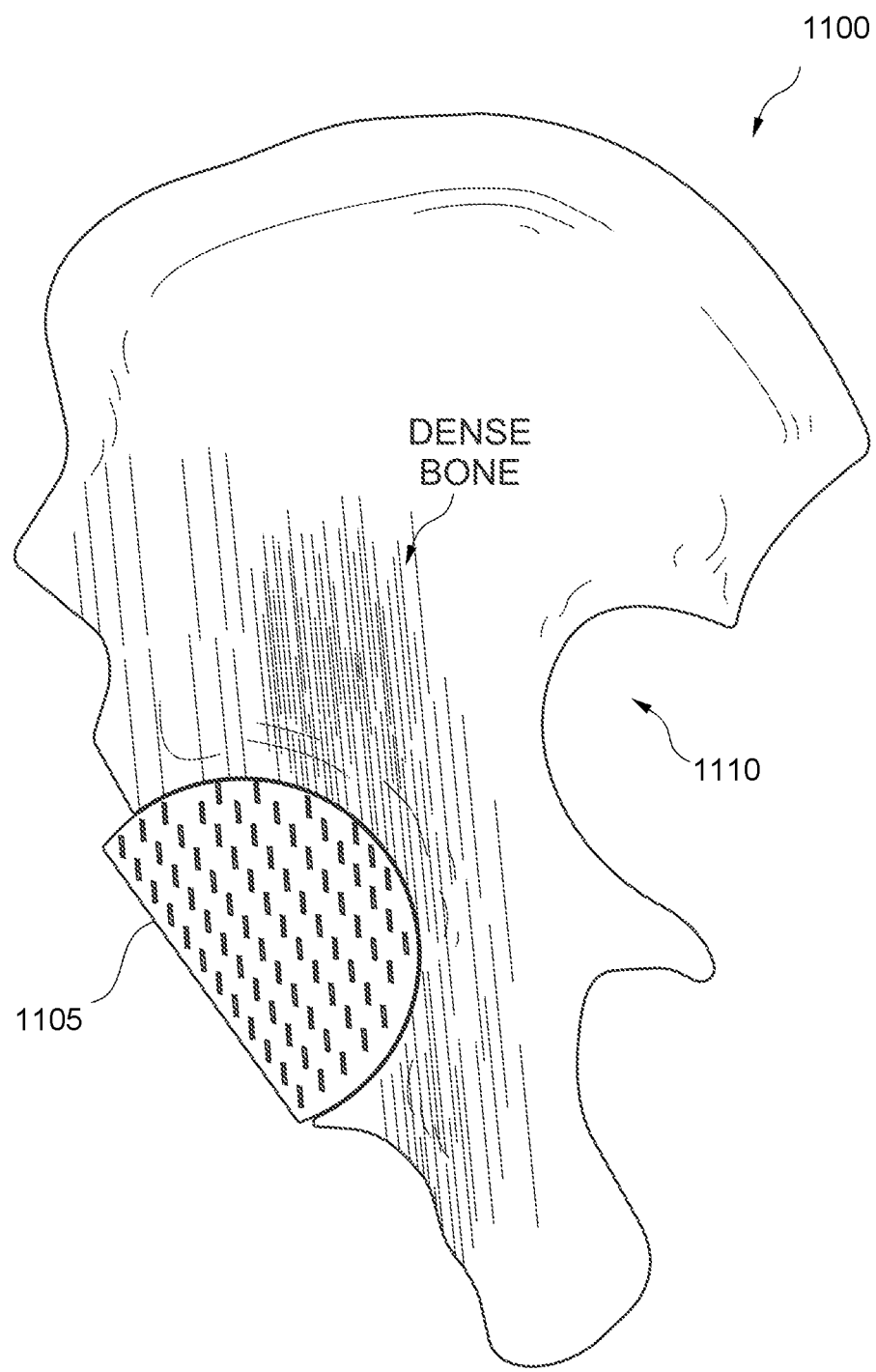
FIG. 11-FIG. 12 illustrate an improvement to site preparation for an installation of a prosthesis.
Figure 12:
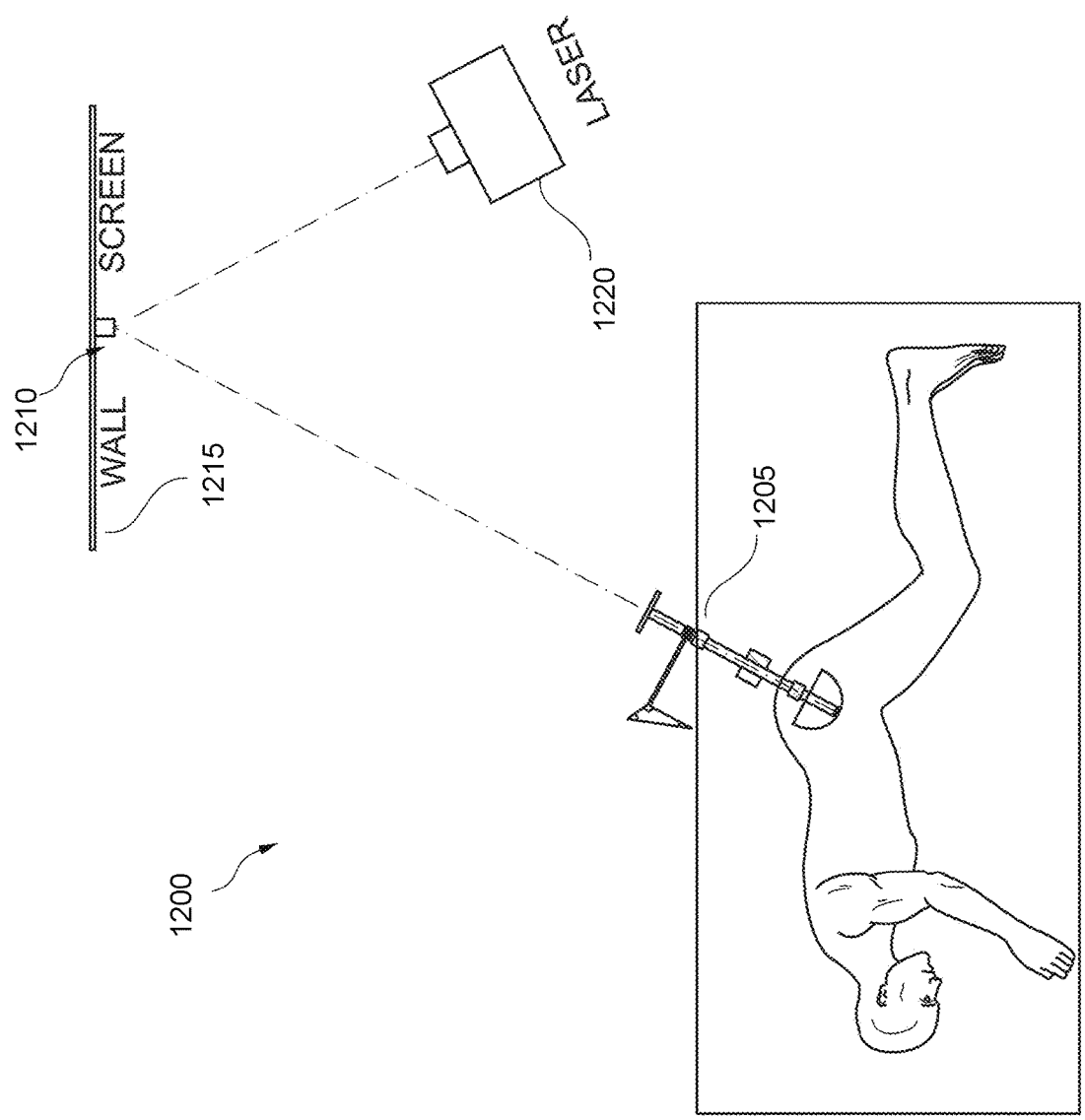

FIG. 11-FIG. 12 illustrate an improvement to site 1100 preparation for an installation of a prosthesis 1105. FIG. 11 illustrates an environment 1100 in which prosthesis 1105 is installed highlighting a problem with site preparation for a prosthesis installation procedure having variable density bone (line thickness/separation distance reflecting variable bone density) of acetabulum 1110.

There is a secondary problem with the process of acetabular preparation and implantation that leads to cup malalignment. Currently, during the process of acetabular reaming, surgeons make several assumptions. One common assumption is that the reamer is fully seated in a cavity and surrounded on all sides by bone. Another common assumption is that the bone that is being reamed is uniform in density. Imagine a carpenter that is preparing to cut a piece of wood with a saw. Now imagine that parts of this piece of wood are embedded with cement and some parts of the piece of wood are hollow and filled with air. The carpenter's saw will not produce a precise cut on this object. Some parts are easy to cut, and some parts are harder to cut. The saw blades skives and bends in undesirable ways. A similar phenomenon happens in acetabular preparation with a reamer and when performing the cuts for knee replacement with a saw. With respect to the acetabulum, the side of the cavity that is incomplete (side of the reamer that is uncovered) will offer less resistance to the reamer and therefor the reamer preferentially reams towards the direction of the uncovering. Second, the reamer cuts the soft bone much more easily than the dense and sclerotic bone, so the reamer moves away from the sclerotic bone and moves toward the soft bone. From a machining perspective, the reaming and preparation of the acetabulum may not be concentric or precise. This may be a significant factor in the surgeon's inability to impact the cup in the desired location FIG. 12 illustrates an alignment system 1200 for preparation and installation of a prosthesis to help address/minimize this effect. A first step that can be taken is to include directionality into the process of reaming at the outset, and not just at the last step during impaction. Current technique allows the surgeon to ream the cup haphazardly moving the reamer handle in all directions, being ignorantly unaware that he is actually creating a preference for the sinking path of the acetabular implant. Ultimately the direction in which the surgeon reams may in fact be determining the position/path of the final implant. The surgeon then impacts the cup using the traditional A-frame or any of the currently used intra-operative measurement techniques such as navigation or fluoroscopy. These methods provide information about the position of the cup either as it is being implanted or after the implantation has occurred. None of these techniques predetermine the cup's path or function to guide the cup in the correct path.

Proposed is a method and a technique to eliminate/reduce this problem. Before the surgeon begins to ream the acetabulum, the reamer handle should be held, with an A-frame attached, in such a way to contemplate the final position of the reamer and hence the implant, (e.g., hold the reamer in 40-degree abduction and 20-degree anteversion reaming is started). This step could also be accomplished with navigation or fluoroscopy. The surgeon could, for example, immediately mark this position on a screen or the wall in the operating room as described below and as illustrated in FIG. 12. After the anticipated position of the reamer is marked, the surgeon can do whatever aspect of reaming that needs to be done. For example, the first reaming usually requires medialization in which the reamer is directed quite vertically to ream in to the pulvinar. Typically, three or four reamings are done. First, the acetabular cavity is medialized. The other reamings function to get to the subchondral bone in the periphery of the acetabulum. One solution may be that after each reaming, the reamer handle be held in the final anticipated position of the implant. In some cases, it may be difficult to have an A-frame attached to every reamer and to estimate the same position of the reamer in the operating space accurately with the A-frame.

An alternative to that is also proposed to address this process. For example, at a proximal end of the reamer shaft handle will be placed a first reference system 1205, for example a laser pointer. This laser pointer 1205 will project a spot 1210 either on a wall or on a screen 1215, a known distance from the operating room table. That spot 1210 on wall 1215 (or on the screen) is then marked with another reference system 1220, for example a second independent laser pointer that sits on a steady stand in the operating room. Thereafter manipulating the shaft handle so that the first reference system has the desired relationship, example coaligned, with the second reference system, the surgeon knows that the device attached to the handle has the desired orientation. So, when the first reamer is held in the anticipated and desired final alignment of the implant (e.g., 40-degree abduction, 20-degree anteversion for many preferred installation angles of an acetabular cup), the laser pointer at the proximal end of the reamer handle projects a spot on the wall or screen. That spot is marked with the second stationary laser and held for the duration of the case. All subsequent reamings will therefore not require an A-frame to get a sense of the proper alignment and direction of the reamer. The surgeon assures that no matter how he moves the reamer handle in the process of reaming of the acetabulum, that the reaming finishes with the reamer handle (laser pointer) pointing to the spot on the wall/screen. In this manner, directionality is assured during the reaming process. In this way the sinking path of the actual implant is somewhat predetermined. And no matter what final intra-operative monitoring technique is used (A-frame, C-Arm, Navigation) that the cup will likely seat/sink more closely to the desired final position.

Figure 13:
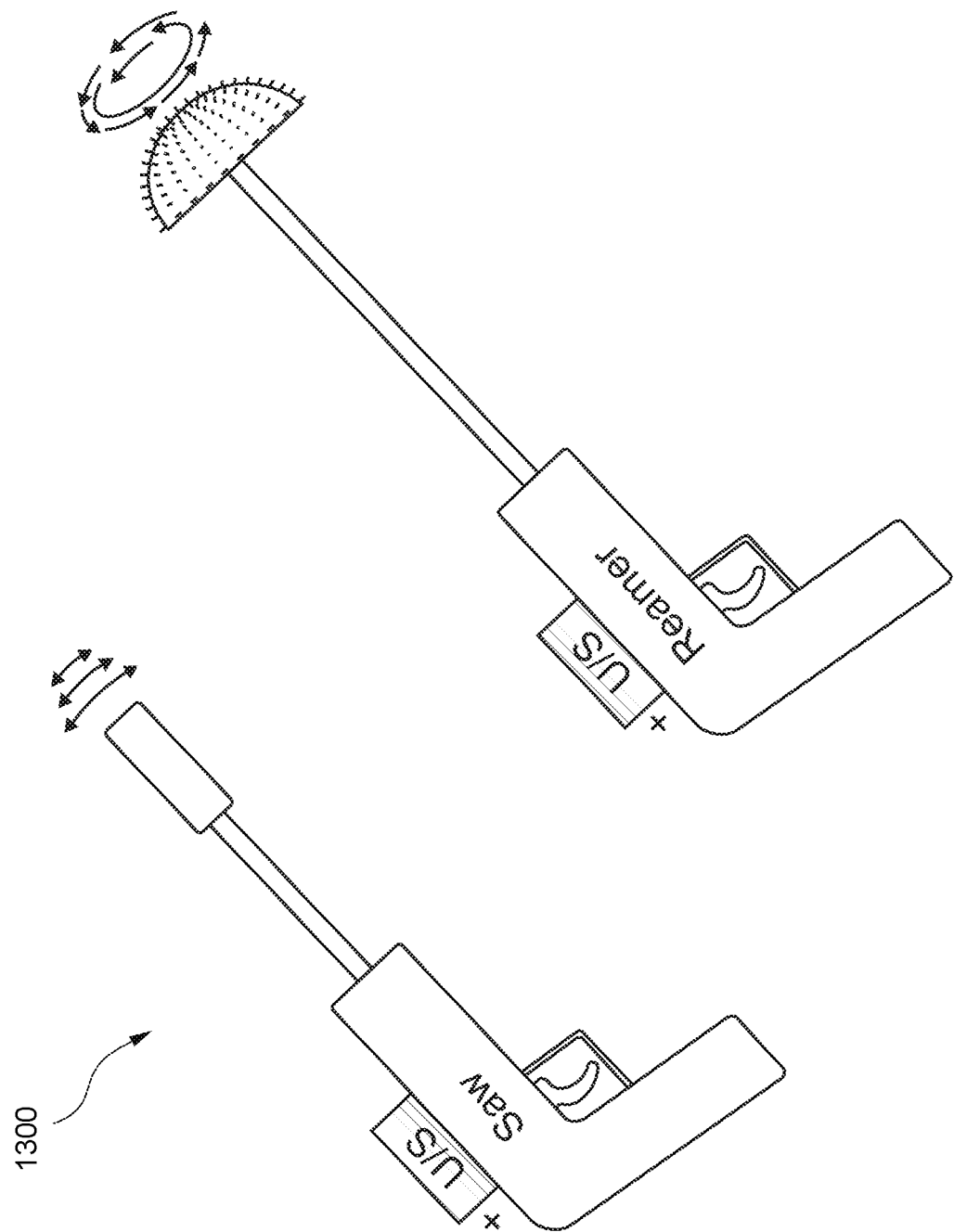
FIG. 13 illustrates modified surgical devices incorporating vibratory energy as at least an aid to mechanical preparation.

FIG. 13 illustrates modified surgical devices 1300 incorporating vibratory energy as at least an aid to mechanical preparation. Also proposed herein is another concept to address a problem associated with non-concentric reaming of the acetabulum caused by variable densities of the bone and the uncovering of the reamer. Imagine the same carpenter has to cut through a construct that is made out of wood, air, and cement. The carpenter does not know anything about the variable densities of this construct. There are two different saws available: one that cuts effectively through wood only, and ineffectively through the cement. Also available is a second saw that cuts just as effectively through cement as wood. Which of these saws would improve a chance of producing a more precise cut? Proposed is a mixing of ultrasonic energy with the standard oscillating saw and the standard reamer. In effect any oscillating equipment used in orthopedics, including the saw, reamer, drill, and the like may be made more precise in its ability to cut and prepare bone with the addition of ultrasonic energy. This may feel dangerous and counterintuitive to some; however, the surgeon typically applies a moderate amount of manual pressure to the saw and reamers, without being aware, which occasionally causes tremendous skiving, bending and eccentric reaming. An instrument that does not requires the surgeon's manual force may be significantly safer and as well as more precise and effective.

A further option includes disposition of a sensor in the shaft of the ultrasonic reamers and saws so that the surgeon can ascertain when hard versus soft bone is being cut, adding a measure of safety by providing a visual numerical feedback as to the amount of pressure being utilized. This improvement (the ability to cut hard and soft bone with equal efficacy) will have tremendous implications in orthopedic surgery. When the acetabular cavity is prepared more precisely, with significantly lower tolerances, especially when directionality is observed, the acetabular implant (cup) may more easily follow the intended sinking path.

Other applications of this concept could be very useful. Pressfit and ingrowth fixation in total knee replacements in particular (as well as ankle, shoulder and other joints to a lesser degree) are fraught with problems, particularly that of inconsistent bony ingrowth and fixation. The fact that a surgeon is unable to obtain precise cuts on the bone may be a significant factor in why the bone ingrowth technology has not gotten off the ground in joints other than the hip. The problem is typically blamed on the surgeon and his less than perfect hands. The experienced surgeon boasts that only he should be doing this operation (i.e.: non-cemented total knee replacement). This concept (a more precise saw that cuts hard and soft bone equally allowing lower tolerances) has huge potential in orthopedics, in that it can lead to elimination of the use of cement in orthopedic surgery altogether. This can spark off the growth and use of bone ingrowth technology in all aspects of joint replacement surgery which can lead to tremendous time saving in the operating room and better results for the patients.

Regarding ultrasonic assisted bone preparation in orthopedics, there is a problem with preparation of bone in joint replacement: these procedures are typically performed using conventional orthopedic equipment such as 1) saw, 2) broach, 3) reamer, and 4) burr.

Figure 14:
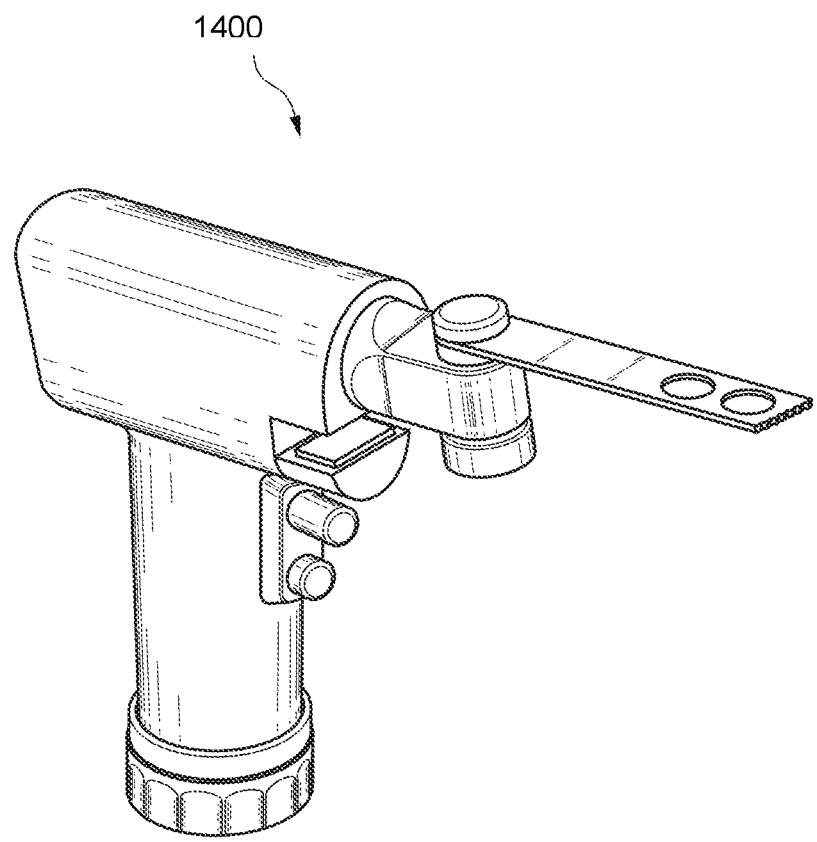
FIG. 14-FIG. 17 illustrate a set of standard orthopedic bone preparation tools.
Figure 15:
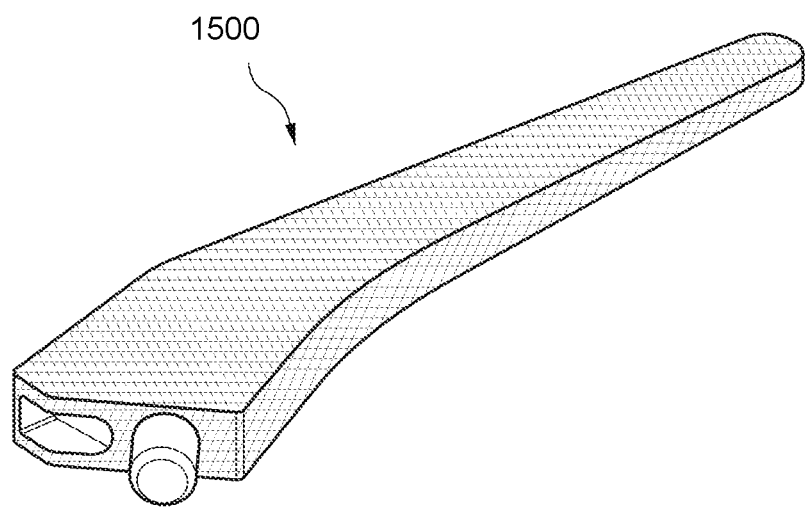
Figure 16:
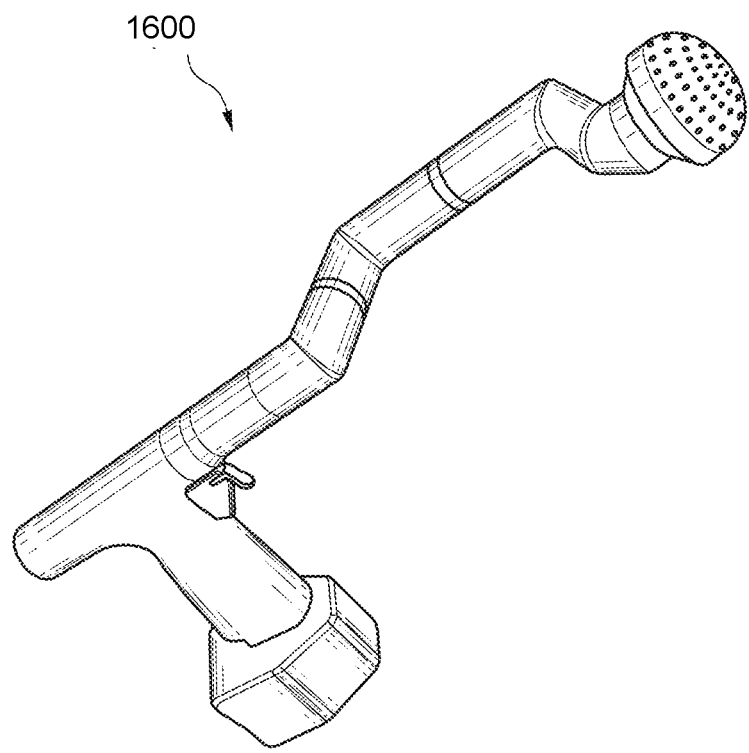
Figure 17:
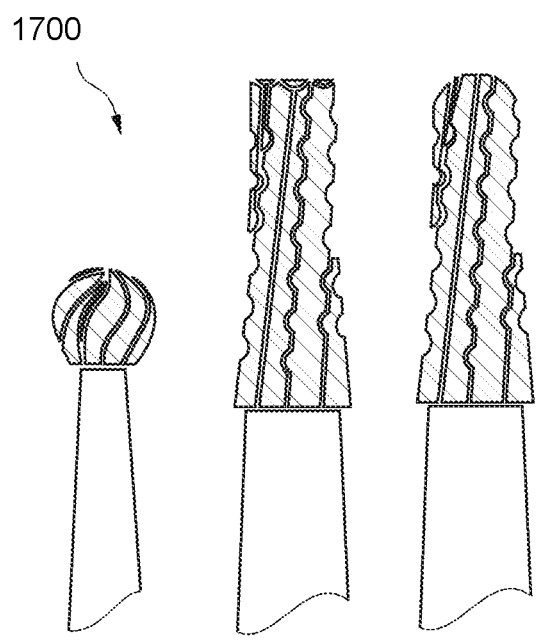

FIG. 14-FIG. 17 illustrate a set of standard orthopedic bone preparation tools, FIG. 14 illustrates a perspective view of a powered bone saw 1400, FIG. 15 illustrates a broach attachment 1500 for a powered reciprocating bone preparation tool, FIG. 16 illustrates a hand-operated reamer 1600, and FIG. 17 illustrates a set of bone preparation burrs 1700. Conventionally, these tools include an operating motion with one degree of freedom (e.g., saw 1400 has a blade that moves laterally, broach attachment 1500 reciprocates longitudinally, reamer 1600 and burrs of set of burrs 1700 each rotate about a longitudinal axis).

As noted below, these bone preparation tools may be enhanced by adding an additional vibratory motion component, preferably but not necessarily required, that is "orthogonal" to the conventional cutting motion. Saw 1400 includes a laterally reciprocating cutting blade that may be ultrasonically enhanced by an additional ultrasonic vibratory motion in one of the other five degrees of motion (e.g., vertical, longitudinal, or vibratory rotations of the blade such as pitch, yaw, and/or roll). Similarly, each of the conventional tools has a primary mode of freedom of motion for the bone processing and an enhancement may be made by adding an additional vibratory motion in one or more other modes of freedom. Embodiments of the present invention may include an additional vibratory motion, in the primary mode and/or the additional mode(s) that may be imperceptible visually (a very small amplitude and/or very fast about or beyond 20,000 hertz).

During bone preparation, two types of bony surfaces are generally encountered which include flat surfaces and contained surfaces. For the flat surfaces, seen in knee replacement, (end of the femur or the top of the tibia) saw 1400 is used to cut the bone. For the contained surfaces (such as the acetabulum and the proximal femur), as in hip replacement surgery, broach attachment 1500 or reamer 1600 is used to prepare the bone.

A problem with all of these techniques is that the density of the bone is not uniform between patients and even within the same compartment or joint of a single patient. The bone can be very soft or very hard and vary from region to region. With hard bone, saw 1400 may "skive" which causes an uneven cut surface and which minimizes that chance of successful "porous ingrowth". This fact may be a principle reason that cement is still used in knee replacement. For the contained bone cavities such as the acetabulum and proximal femur a "goldilocks" situation exists. During preparation, a surgeon may desire to know how with confidence to prepare the bone to provide just the right amount of compressive (fit). Not too loose and not too tight. Too loose leads to loosening and potential infection of the prosthesis. Too tight leads to either poor seating (which can lead to failure of fixation) or fracture (which leads to loss of press fit fixation and loosening).

Current art does not provide a reliable and consistent tool or method for the orthopedic surgeon to reliably prepare a (variable density bone) in order to obtain a "perfect" fit for the prosthesis, whether the bone is flat as in the tibia in knee replacement or contained as in the acetabulum in hip replacement.

For contained cavities such as the acetabulum, U.S. patent application Ser. No. 15/234,782 filed 11 Aug. 2016 (all the content hereby expressly incorporated by reference thereto in its entirety) described a basic estimation of the compressive forces involved in bone. This was named a compressive force and developed an FR curve where FR is related Fn. Us; where Fn represents the normal forces and Us represents the coefficient of static friction. Vis a vis Hooke's law the FR=K. x. Us. Where K represents the material properties of bone (the spring like quality of bone) and x represents the amount of under-reaming of bone compared to an oversized prosthesis intended for press fit.

This current discussion mostly concerns itself with the variable "x" which represents the spring like quality of bone. In Hooke's law F=k. x; k is the spring's constant and x is amount of stretch placed on the spring. In orthopedic bone preparation k is represented by the material properties of bone and x is represented by the difference between the diameters of the prepared bone versus the prosthesis to be press fit.

As we have stated in the earlier papers, the surgeon and industry both appear to have a poor understanding of the basic science of the prosthesis/bone cavity interaction. It is believed that x can be more tightly and precisely machined to give a better tuning of the bone, which is to accept an oversized prosthesis.

BMD3 bidirectional vibratory tool for preparation of bone, and in particular the acetabular cavity: The use of an Acetabular Broach: a new idea. BMD3 bi-directional vibratory tool can be used for preparation of bone (any cavity of bone that needs to be prepared for application of a prosthesis, but especially the acetabulum, as well as the proximal femur, proximal tibia, proximal humerus, and any other long bone in the body that receives a prosthesis). With regards to the acetabulum, unlike the other bones discussed above, this structure has never before been prepared with a broach, but rather always prepared with a hemispherical "cheese grater type" reamers that rotates in one direction (forward). We are proposing that the acetabulum be prepared with a broach using one of the two degrees of freedom for oscillation (1. Longitudinal and 2. rotational), utilizing a bidirectional BMD vibratory tool. The outer surface of this broach will very closely resemble the rough surface of the prosthesis, with high coefficient of static friction. We have seen this method in action in our experiments, particularly at higher frequencies of around 300 hertz, and believe that this method of acetabular preparation will provide a cut surface that is much more precise and conferring the ability to produce lower tolerances. This method may also allow preparation of acetabular cavity in "half" sizes. Currently the cavity is reamed in 1 mm intervals. It may be much easier to prepare the acetabulum with ½ mm interval broaches than ½ mm reamers. Half size broaching may dramatically improve the ability of the surgeon to cut and prepare the acetabular precisely and at lower tolerances.

For purposes of review we recall the equation FR=K. x. Us. Where x is represents the amount of under reaming and the shape of the cup being inserted.

X is controlled by the amount of under or over reaming of the acetabulum. In the past when the surfaces of the cup were not as rough (lower coefficient of static friction, i.e. Zimmer Fiber Metal cup), surgeons used to under ream by 2 mm. Now most companies recommend under reaming by 1 mm, since the surfaces of most cups are much rougher with better porosity characteristics that allow better and quicker bony ingrowth. Sometimes when the surgeon has difficulty seating the cup, he/she reams line to line, and describes this action as "touching up the rim". This action however, many times, eliminates the compressive quality of the acetabulum by decreasing the value of x towards zero. This issue brings attention to the problem that we have described which is that the surgeon does not have anything but a most basic understanding of the spring like qualities of bone. If he/she is can understand the basic science involved in this system, he can then use the proper tools to appropriately fine tune the pelvis for a good press fit fixation, without fear of under seating or fracture. There is a huge market need for better tools to prepare (fine tune) the acetabulum, for good press fit fixation.

Current techniques utilize 'cheese grater type' hemispherical reamers to prepare the bed of the acetabulum. As discussed in our BMD4 paper the quality of acetabular bone can be drastically different between patients and even within the same patient, particularly at different locations around the acetabular fossa. Some parts of the bone are soft, and some are hard. Current cheese grater hemispherical reamers come in 1 mm intervals. This creates two specific problems:
1. The current acetabular reamers in 1mm intervals for preparation of the acetabular bone do not provide the ability to precisely machine the acetabulum, and obtain lower tolerances, and therefore proper tuning of the pelvic bone. 2. No method exists to cut hard and soft bone with the same level of effectiveness, i.e.: hard bone always pushes the reamers towards the soft bone which ends up being chewed up more, and in that sense, a perfect hemisphere is not created with current cheese grater reaming techniques. We therefore are proposing two distinct and separate solutions which we believe can remedy this problem of poor-quality acetabular preparation.

1. The creation of half reamers. The production and use of half reamers give the surgeon the ability to ream up or down by half millimeters. Which gives him/her the ability to fine tune x more precisely, and therefore FR more precisely. This basically gives the surgeon a better set of tuning forks to obtain better tension for the acetabulum and utilize its viscoelastic properties to his/her advantage to obtain a better press fit fixation.

2. Ultrasonic assisted reaming or broaching: Lastly, we believe that there is some room for creating a better cutting tool by adding ultrasonic energy to either the acetabular broach described above, or the acetabular half reamers described above to create an ultrasonic assisted reaming or broaching of the acetabulum for obtaining a more precise cut and at a lower tolerance. We believe this is a new and novel idea that can be considered for preparation of the acetabulum for obtaining better tension of the pelvis for application of an acetabular prosthesis.

The following further elaborates upon ultrasonic assisted preparing, milling, burring, sawing, broaching, reaming, and the like in order to obtain a more precise and efficient process of bone preparation in joint replacement surgery.

Another important advance in orthopedics is the use of robotics in the operating room. Sensors and computer-controlled electromechanical devices are integrated into a robot with a haptic sense, where robotic manipulators now have a complete spatial sense of the patient's bone in the operating room, sometimes to within a half millimeter of accuracy.

Currently robots such as the Stryker Mako robot use a standard rotating burr, reamer or a standard saw to prepare the bone for application of a knee or hip prosthesis. The term "robot" has a special meaning in the context of preparation of live bone in a living patient. Currently it is impermissible to automate any cutting of the live bone. Robot in this sense operates as a realtime constraint that provides haptic feedback to the surgeon during use when certain movements of the processing tool are outside predetermined limits.

An advantage of the robot is that it is helps in processing bone to within less than half a millimeter. This means that the surgeon cannot easily push the burr, reamer or saw out of the allowed haptic plane. In a sense, with the robot, the cutting tool is in safer hands. These standard tools (burr, saw, reamer) provide no particular advantage for the robotic system, that is, the conventional robotic system uses conventional tools with the constraint haptic system. A disadvantage of the robot is that the process of cutting bone with a burr, saw and reamers are very inefficient (slow) especially in hard sclerotic bone. The robot is also very a bulky piece of equipment that adds time to the operation. Mako or other robotic knee surgeries have been somewhat adopted in the uni-compartmental knee replacement procedures (less than 10% of surgeons) and is currently being investigated for use in total knee replacement (Not yet in general markets). The use of the Mako robot in hip replacement however, has shown a very poor adoption rate; less than 0.01% of surgeons have used the Mako robot for hip replacement. Some of the weakness of this robotic procedure is in the process of 1. bone preparation and 2. the actual insertion of the prosthesis into bone.

Earlier tools have addressed tools for installing an acetabular cup into the bony cavity with either "vibratory-BMD3" technique or "discrete impact-BMD4" technique. These solutions are believed to largely eliminate the problems associated with insertion of the prosthesis, providing the ability not only to insert but also to position the prosthesis in proper alignment. Other tools have dealt with manipulating the value of Us, coefficient of static friction, during a process of insertion.

An embodiment of the present invention may include a better job of preparation of bone. In effect, some embodiments provide a tool or process that more precisely manipulates the value of x in the formula: FR=K. x. Us. A goal of some embodiments of the present invention is to obtain lower (tighter tolerances) and do it more quickly, with different tools and methods such as disclosed herein.

An embodiment of the present invention may include bone preparation using robotic surgery through use of haptic control and management to provide an unprecedented level of safety and accuracy coupled with modified equipment that more efficiently prepares in-patient bone while offering novel solutions for bone preparation. In some of these implementations the robotic haptic feedback may be exploited by addition and utilization of a more powerful and efficient bone cutting tool/method never before used or contemplated in orthopedics as it would have been too easy to mis-process a bone portion.

Ultrasonic motion may be added to traditional bone processing tools (e.g., to the tools of FIG. 14-FIG. 17) to offer effective non-traditional bone processing tools. This addition of ultrasonic energy to standard cutting, milling, reaming, burring and broaching techniques can be used to provide (methods and tools) in orthopedic surgery to remove bone more effectively with a (higher material removal rate) MMR and with significantly less force, and therefore more efficiency.

Specifically, in hip replacement surgery the traditional reamer, broach or burr can each be equipped with an ultrasonic transducer to provide an additional ultrasonic vibratory motion (e.g., longitudinal axial ultrasonic vibration). These new cutting methods can then be incorporated within, or in association with, a robot that only allows operation of the tool within safe haptic zones. This ultrasonic robotic cutting tool is therefore more powerful, fast and precise. It would cut hard and soft bone with equal efficiency. Additionally, the robotic operation of an ultrasonic assisted cutting tool is safe, in that the robot does not allow operation of the tool outside of the haptic safe planes.

For example, a Mako robot may be equipped with a rotatory ultrasonic bone preparation tool, operating a bone processing tool (such as single metal-bonded diamond abrasive burr) that is ultrasonically vibrated, for example in the axial direction while the burr is rotated about this axis. This tool can prepare both the proximal femur and acetabulum quickly with extreme precise. This tool and method therefore do away with the standard manual broaching techniques used for femoral preparation and the standard reaming techniques used for acetabular preparation.

An implementation of this system of a constrained ultrasonic vibration of a bone processing tool such as a rotating burr enables a three-dimensional bone-sculpting tool or a smart tool robot. The sculpting tool and smart tool robot may allow a surgeon to accurately, quickly, and safely provide non-planar contours when cutting bones as further described below while also potentially replacing all the conventional preparation tools of FIG. 14-FIG. 17.

The addition of the ultrasonic bone preparation tool to a robot makes the system a truly efficient and precise tool. The surgeon can sculpt the surfaces of the bone, for example a femur, tibia or an acetabulum and the like, and in some implementations any tissue may be sculpted with the sculpting tool, with high degree of accuracy and speed.

With current tools, it would take too much time to perform such bone preparation with a burr, making the operation extremely slow and adding risk to the patient and is therefore not performed. Some implementations include an addition of an improved bone processing tool to any haptically constrained system will make the preparation of bone for joint replacement easy, fast and efficient, ultimately delivering on the promise of a better, faster and more precise operation.

With respect to knee and shoulder replacement, some of the bone surfaces are flat which have led to prosthetic designs that have a flat undersurface, and the decision to prepare these bones with a saw. One concept is to add ultrasonic axial vibrations to the saw for a more effective cut.

Ultrasonic enhancement may be added to all current bone removal techniques in orthopedics, including the burr, saw, reamer, and the broach, making all of these bone preparation tools more effective.

In some instances, use of the same burr described above (e.g., a rotating tool with metal-bonded diamond abrasives that is ultrasonically vibrated in the axial direction) to prepare surfaces of the tibia, femur and the glenoid in the shoulder for mating to an implant surface. One important benefit of use of such a burr is that the surgeon and the smart tool robot can now very quickly and effectively machine these mating surfaces any way desired, potentially introducing waves and contours that can match the undersurface of the prosthesis (which itself has been created with waves and contours for additional stability. Portions of the tibia and the glenoid in the shoulder are flat bones that do not have inherent stability. These bones are prepared in such a way to accept a prosthesis with a flat surface. With the advent of high-power 3D bone sculpting, 3D printing, and smart tool haptic constraint, the sculpting/smart tool system may create prostheses that have waves and contours on their bottom surface to enhance stability when mated. For example, a bone surface may be 3D sculpted/contoured and a prosthesis produced to match the profile, or a preformed contoured prosthesis may be provided with a non-flat profile and the mating bone surface may be sculpted/contoured to match the preformed non-flat prosthesis mating surface, particularly for the "flat ended" bone and the associated prostheses. These contouring profiles for bone and implant mating surfaces are not limited to "flat ended" bones and may have benefit in other implants or bone mating surface.

These changes can enhance the initial fixation of the prosthesis to bone by creating contact surface areas which are more resistant to shear forces. This may provide a specific advantage for the tibial component in knee and the glenoid component in shoulder replacement surgery. These prostheses generally have flat undersurfaces and are less inherently stable. They can be made significantly more stable with the suggested changes in the method of bone preparation and prosthesis fabrication.

FIG. 18 illustrates a side view of a first set of components 1800 for a conventional bone preparation process and FIG. 19 illustrates a side view of a second set of components 1900 for a three-dimensional bone sculpting process that may be enabled by some embodiments of the present invention.

Components 1800 include a bone B (e.g., a tibia) having a flat end 1805. Flat end 1805 is typically removed by a conventional version of saw 1400, to allow an implant 1810 to be installed. In the conventional process, bone B is prepared having a flat/planar bone mating surface 1815 which matches a flat/planar implant mating surface 1820 of implant 1810. As noted, the pair of mated surfaces may exhibit instability, especially with lateral shear loading.

Components of 1900 include bone B that has been prepared differently by removing flat end 1805 using an orthopedic sculpting system as described herein. The sculpting system enables use of an implant 1905 that includes a contoured (non-flat/planar) implant mating surface 1910. A bone mating surface 1915 produced by the orthopedic sculpting system is contoured to match/complement implant mating surface 1910. Components 1900 may include a preformed implant 1905 and surface 1915 is sculpted to match/complement for bonding or surface 1915 is sculpted and surface 1910 is thereafter formed to match/complement surface 1915. An additive/subtractive manufacturing process may be used to make surface 1910 and/or implant 1905. For example, implant 1905 may include two portions—a premade head portion and a later-formed body portion that may be contoured or manufactured as needed to produce surface 1910, with the head portion and body portion joined together to produce implant 1905

Bone ingrowth technology has not enjoyed that same success in shoulder and knee replacement surgery as it has done in hip replacement surgery. One reason that this may be true is because current methods do not allow precise and uniform preparation of bone due to variable density of bone, and especially on the flat surfaces. The ultrasonic assisted bone preparation (example, the orthopedic sculpting system or smart tool robot) discussed herein has a potential to solve this problem of inconsistent bone preparation. The use of the above bone preparation method/tools instead of the standard techniques may represent a disruptive technology. The ability to quickly machine bone, and to do it in an extremely precise and safe manner may eliminate the need for bone cement in joint replacement surgery. This fact can cause an explosion in the use of porous ingrowth prosthesis/technology in orthopedics joint replacement surgery.

Figure 20:
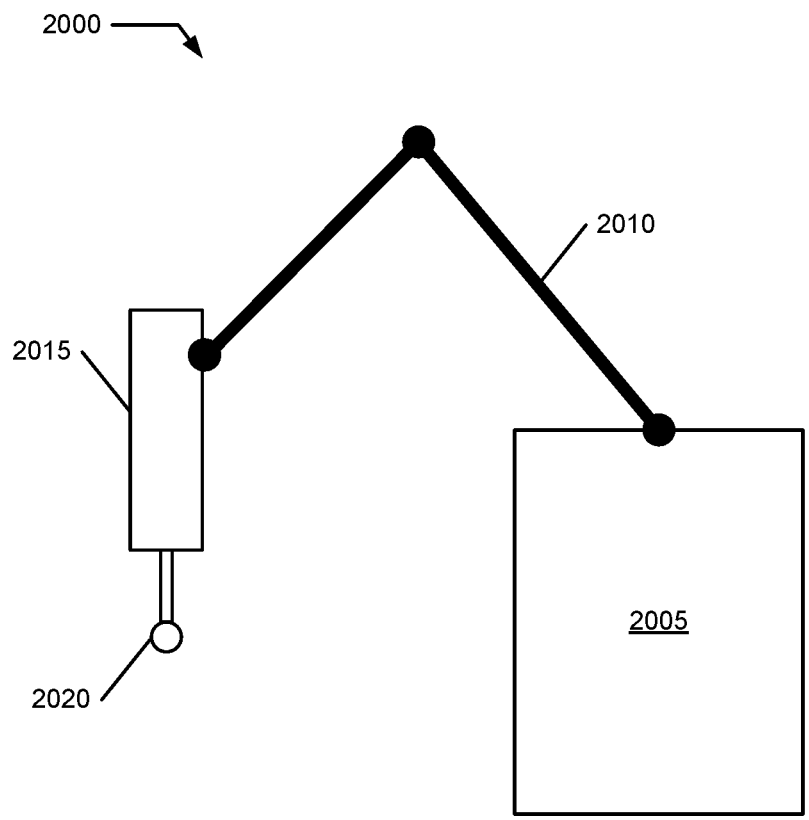
FIG. 20 illustrates a plan diagram of a smart tool robot.

FIG. 20 illustrates a plan diagram of a smart tool robot 2000 which may include a type of three-dimensional bone sculpting tool. Robot 2000 includes a controller 2005 coupled to a linkage 2010 which is coupled to a high-efficiency bone preparation tool 2015, with tool 2015 including a bone processing implement 2020. Controller 2005 includes systems and methods for establishing and monitoring a three-dimensional spatial location for implement 2020. Controller 2005 further includes governance systems for linkage 2010. Collectively controller 2005 and linkage 2010 may be a type of constraint, other systems and methods for another type of constraint and providing feedback may be included in some embodiments of the present invention.

Linkage 2010, illustrated as including a mechanically limited articulating arm, is coupled to both controller 2005 and tool 2015. In some cases when processing a particular in-patient bone, controller 2005 may predefine a set of bone regions of the in-patient bone for a processing (e.g., a cutting, a removing, a reaming, a sawing, a broaching, a burring, and the like). Controller 2005 may monitor a relative location of implement 2020 relative to a particular portion of the in-patient bone to be processed and compare that particular portion with the predefined regions. Those predefined regions may include a first subset of regions to be processed by implement 2020 and in some cases also include (or alternatively substitute for the first subset) a second subset of regions not to be processed by implement 2020. Controller 2005 provides a realtime feedback to the user regarding an appropriateness or desirability of processing each the particular portion of bone at the location of implement 2020.

In some cases, the realtime feedback may include a realtime haptic signal imparted from controller 2005 through linkage 2010 to tool 2015. That haptic signal may be of sufficient strength to significantly restrict an ability of an operator to casually move implement 2020 to a region of the in-patient bone that is not to be processed, and some cases may essentially prevent or inhibit the locating of implement 2020 to those regions of the in-patient that are not to be processed.

Other feedback signals may be included in addition, or in lieu of, the haptic system. Audio feedback may in some cases be sufficient to provide feedback to an operator.

Tool 2015 may be an embodiment of an ultrasonically enhanced bone preparation tool which operates implement 2020. Tool 2015 includes a motive system that operates implement 2020 with a bone processing motion. The bone processing motion includes a primary motion having a primary freedom of motion (e.g., for a burr as illustrated, the primary motion may include a rotation about a longitudinal axis, this primary motion having a freedom of motion that includes the rotation about the longitudinal axis). The bone processing motion includes a secondary motion having a secondary freedom of motion, the secondary freedom of motion different from the first freedom of motion. The secondary motion includes an ultrasonic vibratory motion that enhances the bone-preparation of implement 2020 than would be the case of the primary motion alone.

Different implements and tools may include varying primary and secondary motions, there generally being six freedom of motion possibilities for the primary or secondary motions: x, y, and z translations and rotations about any of the x, y, and z axes. Typically, the primary motion will include a repetitive (and sometimes reciprocating) component.

An operator grips tool 2015 and manipulates it by hand. Controller 2005 automatically monitors these manipulations to establish a relative location of implement 2020 with respect to a particular portion of an in-patient bone. Comparison of the relative location to predetermined/premapped regions of the in-patient bone that identify processable/non-processable regions results in controller 2020 is used to provide appropriate realtime feedback signals to the operator for each particular portion of bone.

The system and methods above have been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A bone preparation tool, comprising:
   a bone-processing implement configured to process an in-patient bone using a primary motion in a primary mode of freedom of motion; and
   a motive system, coupled to said bone-processing implement, configured to operate said bone-processing implement in said primary mode of freedom of motion and in a secondary mode of motion, wherein said primary mode of freedom includes a non-ultrasonic motion and wherein said secondary mode of freedom includes an ultrasonic vibratory motion superimposed on said non-ultrasonic motion; and
   wherein said bone-processing implement includes a femoral broach and wherein said primary mode of freedom of motion includes a longitudinally reciprocating motion.

2. The bone preparation tool of claim 1 wherein said primary mode of freedom of motion includes a subsonic motion for said primary motion.

3. The bone preparation tool of claim 1 further comprising:
   a constraint, coupled to said processing implement, configured to predefine a set of bone regions for said in-patient bone and further configured to monitor a relative location of said processing implement relative to a particular portion of said in-patient bone to be processed by said processing implement;
   wherein said constraint provides a realtime feedback signal during bone processing regarding a desirability of processing said particular portion of said in-patient bone.

4. The bone preparation tool of claim 3 wherein said constraint includes a haptic robotic system and wherein said realtime feedback signal includes a realtime tactile cue that varies responsive to said particular portion.

5. The bone preparation tool of claim 3 wherein said wherein said set of bone regions includes a first subset of desirable bone regions to be processed.

6. The bone preparation tool of claim 5 wherein said realtime feedback signal limits processing of said particular portion when said particular portion is not part of said first subset of desirable bone regions to be processed.

7. The bone preparation tool of claim 4 wherein said constraint includes a haptic robotic system and wherein said realtime feedback signal includes a realtime tactile cue that varies responsive to said particular portion.

8. The bone preparation tool of claim 5 wherein said constraint includes a haptic robotic system and wherein said realtime feedback signal includes a realtime tactile cue that varies responsive to said particular portion.

9. The bone preparation tool of claim 1 wherein said secondary mode of freedom is different from said primary mode of freedom.

10. A method for preparing an in-patient bone, comprising:

processing, using a bone-processing implement, the in-patient bone using a primary motion in a primary mode of freedom of motion for said bone-processing implement; and concurrently operating said bone-processing implement in a secondary motion including a secondary mode of freedom of motion;

wherein said primary motion consists essentially of a non-ultrasonic motion;

wherein said secondary motion includes an ultrasonic vibration motion; and wherein said bone-processing implement includes a femoral broach and wherein said primary mode of freedom of motion includes a longitudinally reciprocating motion.

11. The method of claim 9 further comprising:

constraining said processing using a constraint system coupled to said processing implement not to process undesired portions of the in-patient bone wherein said constraint system identifies a set of desirable regions of the in-patient bone to be processed using said processing implement.

* * * * *